United States Patent [19]

Hirano et al.

[11] Patent Number: 4,859,579
[45] Date of Patent: Aug. 22, 1989

[54] SILVER HALIDE PHOTOGRAPHIC MATERIAL

[75] Inventors: Shigeo Hirano; Tetsuro Kojima; Mitsuru Yamamoto; Noriyuki Inoue; Tatsuo Heki, all of Kanagawa, Japan

[73] Assignee: Fuji Photo Film Co., Ltd., Kanagawa, Japan

[21] Appl. No.: 149,271

[22] Filed: Jan. 28, 1988

[30] Foreign Application Priority Data

Jan. 28, 1987 [JP] Japan ................................. 62-17984

[51] Int. Cl.$^4$ ........................ G03C 1/10; G03C 1/485
[52] U.S. Cl. .................................... 430/598; 430/600; 430/940
[58] Field of Search ..................... 430/598, 940, 600

[56] References Cited

U.S. PATENT DOCUMENTS 4,115,122  9/1978  Adachi et al. ...................... 430/598
4,471,044  9/1984  Parton et al. ....................... 430/598

FOREIGN PATENT DOCUMENTS 62-206545  9/1987  Japan .
62-210451  9/1987  Japan .

Primary Examiner—Paul R. Michl
Assistant Examiner—Mark R. Buscher
Attorney, Agent, or Firm—Sughrue, Mion, Zinn, Macpeak & Seas

[57] ABSTRACT

A silver halide photographic material comprising a support having thereon at least one light-sensitive silver halide photographic emulsion layer, wherein at least one layer selected from the emulsion layer and other hydrophilic colloid layers contains at least one alkynyl substituted heterocyclic quaternary ammonium salt represented by the following general formula (I):

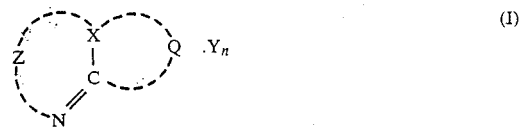

wherein Z represents a non-metallic atomic group necessary to form a substituted or unsubstituted 5-membered or 6-membered heterocyclic ring to which a aromatic ring or a heterocyclic ring may further be condensed; $R^1$ represents a substituted or unsubstituted aliphatic group; X represents

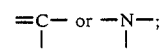

Q represents a non-metallic atomic group necessary to form a substituted or unsubstituted 4-membered to 12-membered non-aromatic hydrocarbon ring or substituted or unsubstituted non-aromatic heterocyclic ring; at least one of $R^1$, a substituent for Z and a substituent for Q includes an alkynyl group; Y represents a counter ion necessary for charge balance; and n represents a number necessary to balance the charge.

11 Claims, No Drawings

SILVER HALIDE PHOTOGRAPHIC MATERIAL

FIELD OF THE INVENTION

The present invention relates to a silver halide photographic material and, more particularly, to silver halide direct positive photographic materials mainly forming latent images in the interior of silver halide grains and negative type silver halide photographic materials mainly forming latent images on the surface of silver halide grains, each of which contains a novel nucleating agent.

BACKGROUND OF THE INVENTION

Nucleating agents have been hitherto employed in silver halide photographic materials for various purposes. For instance, hydrazines, which have been most frequently employed as nucleating agents, have been used as nucleus forming agents in internal latent image type direct positive silver halide emulsions and also have been used for the purpose of increasing sensitivity and/or gradation in negative type surface latent image forming silver halide emulsions.

Silver halide emulsions in which light-sensitive nuclei are mainly present in the interior of silver halide grains and wherein latent images are mainly formed in the interior portion of the grains are called internal latent image type silver halide emulsions, as distinguished from silver halide grains which mainly form latent images on the surface of the grains.

Methods for obtaining direct positive images upon surface development of an internal latent image type silver halide photographic emulsion in the presence of a nucleating agent, and photographic emulsions or light-sensitive materials to be used for such methods are generally known, and described, for example, in U.S. Pat. Nos. 2,456,953, 2,497,875, 2,497,876, 2,588,982, 2,592,250, 2,675,318, 3,227,552 and 3,317,322, British Patents 1,011,062, 1,151,363, 1,269,640 and 2,011,391, Japanese Patent Publication Nos. 29405/68 and 38164/74, Japanese Patent Application (OPI) Nos. 16623/78, 137133/78, 37732/79, 40629/79, 74536/79, 74729/79, 52055/80 and 90940/80 (the term "OPI" as used herein means an "unexamined published application"), etc.

In the above described methods for obtaining direct positive images, while nucleating agents may be added to a developing solution, it is more common to add the nucleating agents to photographic emulsion layers or other appropriate layers of light-sensitive materials.

Hydrazine compounds are most widely known as nucleating agents which are added to silver halide photographic light-sensitive materials. In general, hydrazine type nucleating agents are excellent as to some important properties, such as sensitivity discirmination, since they provide a large difference between maximum density (Dmax) and minimum density (Dmin). However, they are disadvantageous because they require processing at a high pH (pH>12).

Nucleating agents which function in processing at a low pH (pH≦12) are known, however, such as heterocyclic quaternary ammonium salts described, for example, in U.S. Pat. Nos. 3,615,615, 3,719,494, 3,734,738, 3,759,901, 3,854,956, 4,094,683 and 4,306,016, British Patent 1,283,835, Japanese Patent Application (OPI) Nos. 3426/77 and 69613/77, etc. Particularly, propargyl- or butynyl-substituted heterocyclic quaternary ammonium salt compounds as described in U.S. Pat. No. 4,115,122 are excellent nucleating agents in view of sensitivity discrimination when used in direct positive silver halide emulsions. However, in silver halide emulsions, particularly those for color photographic light-sensitive materials, sensitizing dyes are usually employed for the purpose of spectral sensitization. In such cases, competitive adsorption of the sensitizing dyes and the heterocyclic quaternary ammonium type nucleating agents onto silver halide grains takes place, and thus, it is necessary to add a large amount of the quaternary ammonium salt type nucleating agents which are of low adsorptivity. In particular, in the case of multilayer color photographic light-sensitive materials, unevenness of density and poor color balance may undesirably occur. Therefore, these compounds are still insufficient.

In order to resolve this problem, quaternary salt type nucleating agents having a silver halide adsorption accelerating thioamido group are disclosed in U.S. Pat. No. 4,471,044. Although the amount to be added necessary to obtain a sufficiently high Dmax is reduced and the decrease in Dmax during preservation at high temperature is controlled by introduction of such an adsorptive group, these effects still do not achieve a fully satisfactory level.

Further, hemicyanine type quaternary salt compounds are described in Japanese Patent Application (OPI) No. 100426/82. However, these compounds also do not achieve a fully sufficient level of nucleating activity.

On the other hand, it is also known that quaternary ammonium salt type compounds may accelerate development in silver halide negative emulsions as described, for example, in U.S. Pat. No. 4,135,931, Japanese Patent Application (OPI) Nos. 114328/77 and 121321/77, German Patent 2,647,940, Belgian Patent 721,568, etc.

SUMMARY OF THE INVENTION

It is, therefore, an object of the present invention to provide a direct positive photographic light-sensitive material which exhibits a sufficient reversal property (i.e., high Dmax and low Dmin) even when processed with a processing solution having a comparatively low pH.

Another object of the present invention is to provide a direct positive photographic light-sensitive material containing a nucleating agent which provides a desired nucleating effect upon a small amount of addition and does not adversely affect spectral sensitization.

Still another object of the present invention is to provide a multilayer color direct positive photographic light-sensitive material which provides uniform density and good color balance and provides good graininess even when processed with an exhausted running solution.

A further object of the present invention is to provide a direct positive photographic light-sensitive material which undergoes less change in photographic properties, such as decrease in Dmax and increase in Dmin, during preservation under high temperature and/or high humidity conditions.

A further object of the present invention is to provide a direct positive photographic light-sensitive material which hardly forms negative images at high light intensity.

A still further object of the present invention is to provide a direct positive photographic light-sensitive material which exhibits high speed development in the early stages of development processing.

A still further object of the present invention is to provide a negative type photographic light-sensitive material having increased photographic sensitivity.

These and other objects of the present invention will become apparent from the following description of the invention and examples thereof.

These objects of the present invention are attained by a silver halide photographic material comprising a support having thereon at least one light-sensitive silver halide photographic emulsion layer, wherein at least one layer selected from the emulsion layer(s) and other hydrophilic colloid layer(s) contains at least one alkynyl substituted heterocyclic quaternary ammonium salt represented by the following general formula (I):

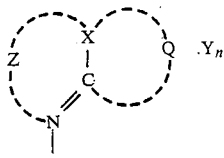 (I)

wherein Z represents a non-metallic atomic group necessary to form a substituted or unsubstituted 5-membered or 6-membered heterocyclic ring to which an aromatic ring or a heterocyclic ring may further be condensed; $R^1$ represents a substituted or unsubstituted aliphatic group; X represents

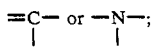

Q represents a non-metallic atomic group necessary to form a substituted or unsubstituted 4-membered to 12-membered non-aromatic hydrocarbon ring or a substituted or unsubstituted non-aromatic heterocyclic ring; at least one of $R^1$, a substituent for Z and a substituent for Q includes an alkynyl group; Y represents a counter ion necessary for charge balance; and n represents a number necessary to balance the charge.

DETAILED DESCRIPTION OF THE INVENTION

While the compound represented by general formula (I) can be incorporated into any emulsion layer(s) or other hydrophilic colloid layer(s) constituting the silver halide photographic material, it is preferred to incorporate the compound into an internal latent image type silver halide photographic emulsion layer or a hydrophilic colloid layer adjacent thereto in the case of a positive type photographic material, or into a surface latent image type silver halide photographic emulsion layer or a hydrophilic colloid layer adjacent thereto in the case of a negative type photographic material.

Now, the compound represented by the general formula (I) is described in detail below.

In general formula (I), at least one of $R^1$, Z and Q may include a group capable of accelerating adsorption onto silver halide grains.

The heterocyclic ring (including the optional condensed ring) which is completed with Z includes, for example, a quinolinium nucleus, a benzimidazolium nucleus, a pyridinium nucleus, an imidazolium nucleus, an indolenium nucleus, a pyrrolinium nucleus, a phenanthridinium nucleus, an isoquinolinium nucleus and a naphthopyridinium nucleus, etc.

The heterocyclic ring (including the condensed ring) which is completed with Z may be substituted. Examples of the substituents include an alkyl group (preferably having from 1 to 18 carbon atoms, for example, a methyl group, an ethyl group, a cyclohexyl group, etc.), an alkenyl group (preferably having from 2 to 18 carbon atoms, for example, a vinyl group, an allyl group, a butenyl group, etc.), an alkynyl group (preferably having from 2 to 18 carbon atoms, for example, an ethynyl group, a propargyl group, a butynyl group, etc.), an aralkyl group (preferably having from 7 to 20 carbon atoms, for example, a benzyl group, etc.), an aromatic group (preferably having from 6 to 20 carbon atoms, for example, a phenyl group, a naphthyl group, etc.), a hydroxy group, an aliphatic oxy group (including an alkoxy group, an alkenyloxy group, an alkynyloxy group, etc., preferably having from 1 to 18 carbon atoms, for example, a methoxy group, an ethoxy group, an allyloxy group, a propargyloxy group, a butynyloxy group, etc.), an aromatic oxy group (preferably having from 6 to 20 carbon atoms, for example, a phenoxy group, etc.), a halogen atom (for example, a fluorine atom, a chlorine atom, a bromine atom, a iodine atom, etc.), an amino group, a substituted amino group (preferably having from 1 to 18 carbon atoms, for example, a methylamino group, a dimethylamino group, a propargylamino group, a phenylamino group, etc.), an aliphatic thio group (preferably having from 1 to 18 carbon atoms, for example, a methylthio group, a propargylthio group, etc.), an aromatic thio group (preferably having from 6 to 20 carbon atoms, for example, a phenylthio group, etc.), an acyloxy group (preferably having from 1 to 18 carbon atoms, for example, an acetoxy group, a benzoyloxy group, etc.), a sulfonyloxy group (preferably having from 1 to 18 carbon atoms, for example, a methanesulfonyloxy group, a toluenesulfonyloxy group, etc.), an acylamino group (preferably having from 1 to 18 carbon atoms, for example, an acetylamino group, a benzoylamino group, etc.), a sulfonylamino group (preferably having from 1 to 18 carbon atoms, for example, a methanesulfonylamino group, a benzenesulfonylamino group, etc.), a carboxyl group, an aliphatic oxycarbonyl group (preferably having from 2 to 18 carbon atoms, for example, a methoxycarbonyl group, a propargyloxycarbonyl group, etc.), an aromatic oxycarbonyl group (preferably having from 7 to 20 carbon atoms, for example, a phenoxycarbonyl group, etc.), an acyl group (preferably having from 1 to 20 carbon atoms, for example, a formyl group, an acetyl group, a benzoyl group, etc.), a carbamoyl group, an N-substituted carbamoyl group (preferably having from 2 to 20 carbon atoms, for example, an N-methylcarbamoyl group, an N-propargylcarbamoyl group, an N-phenylcarbamoyl group, etc.), a sulfamoyl group, an N-substituted sulfamoyl group (preferably having from 1 to 18 carbon atoms, for example, an N-methylsulfamoyl group, an N,N-dimethylsulfamoyl group, an N-butynylsulfamoyl group, an N-phenylsulfamoyl group, etc.), a sulfo group, a cyano group, a ureido group, a substituted ureido group (preferably having from 2 to 20 carbon atoms, for example, a 3-methylureido group, a 3-propargylureido group, a 3-phenylureido group, etc.), a substituted urethane group (preferably having from 2 to 20 carbon atoms, for example, methoxycarbonylamino group, a propargyloxycarbonylamino group, a phenoxycarbonylamino group, etc.), a carboxylic acid ester group (preferably having from 2 to 20 carbon atoms, for example, an ethoxycarbonyloxy group, a propargyloxycarbonyloxy group, a phenoxycarbonyloxy group, etc.) and a substituted or unsubstituted imino group (preferably having up to 18 carbon atoms, for example, an N-methylimino group, an N-propargylimino group, etc.). As the substituent for Z, one or more can be selected, for example, from the above described substituents. When two or more substituents are present, they may be the same or different. The above described substituents such as an alkyl group and an aryl group may further be substituted with one or more of these substituents, if desired.

Specific examples of the heterocyclic rings completed with Z include, for example, (1) as a quinolinium nucleus, a quinolinium nucleus, a quinalidinium nucleus, a lepidinium nucleus, a 6-ethoxyquinaldinium nucleus, and a 6-propargyloxyquinaldinium nucleus, a 2,4-dimethylquinolinium nucleus, a 3-acetylaminoquinolinium nucleus, and a 6-acetylaminoquinaldinium nucleus; (2) as a benzimidazolium nucleus, a 1-ethyl-5,6-dichloro-2-methylbenzimidazolium nucleus, a 1-ethyl-2-methyl-benzimidazolium nucleus, and a 5,6-dichloro-2-methyl-1-phenylbenzimidazolium nucleus; (3) as a pyridinium nucleus, a pyridinium nucleus, a 2-methylpyridinium nucleus, a 2,4,6-trimethylpyridinium nucleus, and a 4-phenylpyridinium nucleus; (4) as an imidazolium nucleus, a 1,2-dimethylimidazolium nucleus, and a 1-ethyl-2,4,5-trimethylimidazolium nucleus; (5) as an indolenium nucleus, an indolenium nucleus, and a 3,3-dimethylindolenium nucleus; (6) as a pyrrolinium nucleus, a 2-methylpyrrolinium nucleus; (7) as a phenanthridium nucleus, a phenanthridium nucleus; (8) as an isoquinolinium nucleus, an isoquinolinium nucleus, and a 5-hydroxyisoquinolinium nucleus; and (9) as a naphthopyridinium nucleus, a 2-methylnaphtho[2,3-β]pyridinium nucleus.

Preferred examples of the heterocyclic nuclei completed with Z include a quinolinium nucleus, a benzimidazolium nucleus, a pyridinium nucleus, a phenanthridinium nucleus, a naphthopyridinium nucleus and an isoquinolinium nucleus. More preferred nuclei are a quinolinium nucleus, a naphthopyridinium nucleus and a benzimidazolium nucleus. A quinolinium nucleus is most preferred.

Preferred examples of the aliphatic group represented by $R^1$ include an unsubstituted alkyl group having from 1 to 18 carbon atoms (for example, a methyl group, an ethyl group, an isopropyl group, a hexadecyl group, etc.), a substituted alkyl group having from 1 to 18 carbon atoms in the alkyl moiety, an alkenyl group (for example, an allyl group, etc.) and an alkynyl group (for example, an ethynyl group, a propargyl group, a 3-butynyl group, a 2-butynyl group, a 4-pentynyl group, a 3-bytyn-2-yl group, a 1-phenylpropargyl group, a 3-phenylpropargyl group, etc.), etc.

The substituents for the alkyl group (when R' is a substituted alkyl group) include those as described above for Z. Examples of the substituted alkyl group include, for example, a sulfoalkyl group (for example, a 2-sulfoethyl group, a 3-sulfopropyl group, a 4-sulfobutyl group, etc.), a carboxyalkyl group (for example, a 2-carboxyethyl group, etc.), a hydroxyalkyl group (for example, a 2-hydroxyethyl group, etc.), an alkoxyalkyl group (for example, a 2-methoxyethyl group, a 2-hydroxyethoxymethyl group, a 2-methoxyethoxy group, etc.), an acyloxyalkyl group (for example, a 2-acetoxyethyl group, etc.), a dialkylaminoalkyl group (for example, a 2-dimethylaminoethyl group, etc.) and an aralkyl group (for example, a benzyl group, etc.), etc.

For $R^1$, a propargyl group is particularly preferred.

Q represents an atomic group necessary to form a 4-membered to 12-membered non-aromatic hydrocarbon ring or non-aromatic heterocyclic ring. These rings may also be substituted with one or more substituents as described above for Z.

Examples of the non-aromatic hydrocarbon ring wherein X represents a carbon atom include a cyclobutane ring, a cyclopentane ring, a cyclopentene ring, a cyclohexane ring, a cyclohexene ring, a cycloheptane ring, a cycloheptene ring, a cycloheptadiene ring, a cyclooctane ring, a cyclooctene ring, a cyclodecane ring, a cyclododecane ring, a cyclododecane ring, a cyclododecene ring, a cyclododecadiene ring, an indan ring and a tetrarin ring, etc.

The non-aromatic heterocyclic ring includes, as a hetero atom, for example, a nitrogen atom, an oxygen atom, a sulfur atom, a selenium atom or a combination thereof.

Examples of the non-aromatic heterocyclic ring wherein X represents a carbon atom include a tetrahydrofuran ring, a tetrahydropyran ring, a butyrolactone ring, a pyrrolidine ring, a piperidine ring, a pyrrolidone ring, a tetrahydrothiophene ring, a tetrahydrothiopyran ring, a tetrahydroselenole ring, a chroman ring and a tetrahydroquinoline ring, etc.

Examples of the non-aromatic heterocyclic ring wherein X represents a nitrogen atom include a pyrrolidine ring, a pyrroline ring, a piperidine ring, a pyridone ring, a perhydrooxazine ring, a perhydrothiazine ring, a piperazine ring, a tetrahydroquinoline ring and an indoline ring, etc.

Preferred examples of the ring completed with Q are those wherein X represents a carbon atom. Particularly, a cyclopentane ring, a cyclohexane ring, a cycloheptane ring, a cyclohexene ring, an indan ring, a tetrahydropyran ring and a tetrahydrothiopyran ring, etc. are preferred for the ring completed with Q.

The alkynyl group which is present in at least one of $R^1$, a substituent for Z or a substituent for Q has been partially described above with respect to substituents for Z and, further, the alkynyl group preferably contains from 2 to 18 carbon atoms and may be an ethynyl group, a propargyl group, a 2-butynyl group, a 1-methylpropargyl group, a 1,1-dimethylpropargyl group, a 3-butynyl group or a 4-pentynyl group, etc.

These alkynyl groups may further be substituted by those substituents which have been mentioned above as substituents for Z. Examples thereof include a 3-phenylpropargyl group, a 3-methoxycarbonylpropargyl group, a 4-methoxy-2-butynyl group or a 3-carboxypropargyl group, etc.

Of these groups, a propargyl group is most preferred as the alkynyl group.

The group capable of accelerating adsorption onto silver halide grains which is present in at least one of $R^1$, Z or Q includes a thioamido group, a mercapto group and a 5-membered or 6-membered nitrogen-containing heterocyclic group. The adsorption accelerating group may be connected to $R^1$, Z or Q in any style. However, it is preferred that the adsorption accelerating group is connected in the form illustrated by the following general formula (II):

$$W + L + m \qquad (II)$$

wherein W represents a group capable of accelerating adsorption onto silver halide grains as defined above; L represents a divalent linking group; and m represents 0 or 1.

Among suitable adsorption accelerating groups, the thioamido group is a divalent group represented by

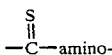

and while it may form a part of a cyclic structure, it is preferably an acyclic thioamido group. Useful thioamido adsorption accelerating groups can be selected from those as described, for example, in U.S. Pat. Nos. 4,030,925, 4,031,127, 4,080,207, 4,245,037, 4,255,511, 4,266,013 and 4,276,364, *Research Disclosure*, Vol. 151, No. 15162 (November, 1976) and ibid., Vol. 176, No. 17626 (December, 1978), etc.

A particularly preferred thioamido group is represented by the following general formula (III)

wherein one of E and E' represents $-N(R^6)-$ and the other represents $-O-$, $-S-$ or $-N(R^7)-$; $R^5$ represents a hydrogen atom, an aliphatic group or an aromatic group, or may be connected with E or E' to form a 5-membered or 6-membered heterocyclic ring; and $R^6$ and $R^7$, which may be the same or defferent, each represents a hydrogen atom, an aliphatic group or an aromatic group.

The thioamido group represented by general formula (III) is a group derived from a thiourea, a thiourethane or a dithiocarbamic acid ester, etc.

Examples of the heterocyclic ring formed by the connection of $R^5$ with E or E' include those heterocyclic rings useful as acid nuclei of merocyanine dyes. Specific examples include 4-thiazoline-2-thione, thiazolidine-2-thione, 4-oxazoline-2thione, oxazolidine-2-thione, 2-pyrazoline-5-thione, 4-imidazoline-2-thione, 2-thiohydantoin, rhodanine, isorhodanine, 2-thio-2,4-oxazolidinedione, thiobarbituric acid, tetrazoline-5-thione, 1,2,4-triazoline-3-thione, 1,3,4-thiadiazoline-2-thione, 1,3,4-oxadiazoline-2-thione, benzimidazoline-2-thione, benzoxazoline-2-thione and benzothiazoline-2-thione, etc. These heterocyclic groups may be substituted.

The mercapto adsorption accelerating group represented by W includes such groups wherein a $-SH$ group is directly connected to $R^1$, Q or Z, as well as groups wherein a $-SH$ group is connected to a substituent for $R^1$, Q or Z. The mercapto group includes an aliphatic mercapto group, an aromatic mercapto group and a heterocyclic mercapto group (the case wherein a nitrogen atom is present adjacent to the carbon atom to which the $-SH$ group is connected has been described above as the ring forming thioamido group which is a tautomer). Examples of the aliphatic mercapto group include a mercapto alkyl group (for example, a mercaptoethyl group, a mercaptopropyl group, etc.), a mercapto alkenyl group (for example, a mercaptopropenyl group, etc.) and a mercapto alkynyl group (for example, a mercaptobutynyl group, etc.). Examples of the aromatic mercapto group include a mercaptophenyl group and a mercaptonaphthyl group. Examples of the heterocyclic mercapto group include a 4-mercaptopyridyl group, a 5-mercaptoquinolyl groups, a 6-mercaptobenzothiazolyl group, etc., in addition to those described above for the ring forming thioamido group.

Suitable 5-membered or 6-membered nitrogen-containing heterocyclic adsorption accelerating groups represented by W include those which comprised with one or more atoms which are selected among a carbon atom, a nitrogen atom, an oxygen atom and a sulfur atom.

Preferred examples thereof include a benzotriazolyl group, a triazolyl group, a tetrazolyl group, an indazolyl group, a benzimidazolyl group, an imidazolyl group, a benzothiazolyl group, a thiazolyl group, a benzoxazolyl group, an oxazolyl group, a thiadiazolyl group, an oxadiazolyl group or a triazinyl group, etc. These groups may have one or more appropriate substituents. Suitable substituents include those which are described as substituents for Z. More preferred examples thereof are a benzotriazolyl group, a triazolyl group, a tetrazolyl group and an indazolyl group. A benzotriazolyl group is most preferred.

Preferred examples of the 5-membered or 6-membered nitrogen-containing heterocyclic group include a benzotriazol-5-yl group, a 6-chlorobenzotriazol-5-yl group, a benzotriazol-5-carbonyl group, a 5-phenyl-1,3,4-triazol-2-yl group, a 4-(5-methyl-1,3,4-triazol-2-yl)benzoyl group, a 1H-tetrazol-5-yl group or a 3-cyanoindazol-5-yl group.

The divalent linking group represented by L in the general formula (II) is an atom or atomic group containing at least one of C, N, S and O. Specifically, L comprises an alkylene group, an alkenylene group, an alkynylene group, an arylene group, $-O-$, $-S-$, $-NH-$, $-N=$, $-CO-$, $-SO_2-$ (these groups optionally having one or more substituents), or a combination thereof. More specific examples of L include (1) an alkylene group (preferably containing 1 to 12 carbon atoms, such as a methylene group, an ethylene group, a trimethylene group, etc.), (2) an alkenylene group (preferably containing 2 to 12 carbon atoms, such as a vinylene group, a butynylene group, etc.), (3) an alkynylene group (preferably containing 2 to 12 carbon atoms, such as an ethylene group, a butynylene group, etc.), (4) an arylene group (preferably containing 6 to 10 carbon atoms, such as a phenylene group, a naphthylene group, etc.), (5) $-O-$, (6) $-S-$, (7) $-NH-$, (8) $-N=$, (9) $-CO-$, (10) $-SO_2-$, and, as combinations thereof, (11)

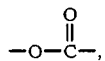

(16) $-NHSO_2NH-$, and appropriate combinations of (1) to (4) (12)

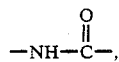

(13) $-NHSO_2-$, (14)

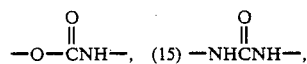

and (5) to (16) (for example,

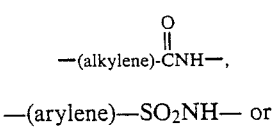

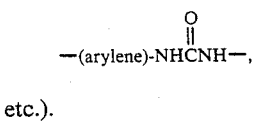

etc.).

The counter ion for charge balance represented by Y is an appropriate anion that can counterbalance the positive charge produced by the quaternary ammonium salt in the heterocyclic nucleus and includes, as a monovalent anion, a bromide ion, a chloride ion, an iodide ion, a p-toluenesulfonate ion, an ethylsulfonate ion, a perchlorate ion, a trifluoromethanesulfonate ion, a thiocyanate ion and a picrate ion, etc. In this case, n represents 1. Examples of a divalent anion include, for example, a sulfate ion, an oxalate ion and a benzene disulfonate ion, etc. In this case, n represents ½. Where the heterocyclic quaternary ammonium salt further contains an anionic substituent such as a sulfoalkyl substituent, the salt may take the form of betaine. In this case, the counter ion is not necessary, and hence n represents 0. Where the heterocyclic quaternary ammonium salt has two anionic substituents such as two sulfoalkyl groups, Y represents a cationic counter ion such as an alkali metal ion (for example, a sodium ion, a potassium ion, etc.) or an ammonium salt (for example, a triethylammonium, etc.).

Of the compounds represented by general formula (I), those represented by the following general formula (IV) are preferred:

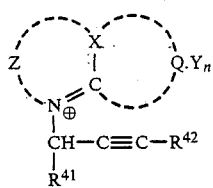

wherein Z, X, Q, Y and n each has the same meaning as defined in general formula (I); $R^{41}$ represents a hydrogen atom or an aliphatic group; and $R^{42}$ represents a hydrogen atom, an aliphatic group or an aromatic group.

Examples of the aliphatic group represented by $R^{41}$ include an alkyl group (preferably having from 1 to 12 carbon atoms, for example, a methyl group, an ethyl group, a hexyl group, etc.), an alkenyl group (preferably having from 2 to 12 carbon atoms, for example, an allyl group, etc.), an aralkyl group (preferably having from 7 to 12 carbon atoms, for example, a benzyl group, etc.) and a cycloalkyl group (preferably having from 4 to 12 carbon atoms, for example, a cyclohexyl group, etc.), etc.

Examples of the aliphatic group represented by $R^{42}$ include those as described for $R^{41}$ above. Examples of the aromatic group represented by $R^{42}$ are preferably those having from 6 to 20 carbon atoms, for example, a phenyl group, a naphthyl group, etc.

The aliphatic group or aromatic group represented by $R^{41}$ or $R^{42}$ may have one or more substituents and they may be selected, for example, from the substituents described above for Z. $R^{41}$ and $R^{42}$ each preferably represents a hydrogen atom.

Further, it is preferred that at least one of Z and Q contains a group capable of accelerating adsorption onto silver halide grains. Examples of the group capable of accelerating adsorption onto silver halide grains include those represented by general formula (II) above.

More preferred compounds among the compounds represented by general formula (IV) are represented by the following general formula (V):

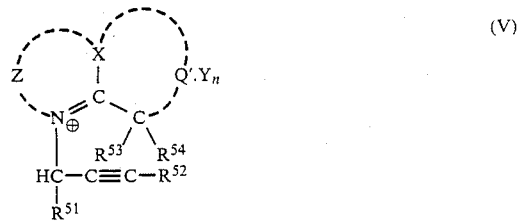

wherein Z, X, Y and n each has the same meaning as defined in general formula (I); $R^{51}$ and $R^{52}$ have the same meanings as $R^{41}$ and $R^{42}$ defined in general formula (IV), respectively; $R^{53}$ and $R^{54}$, which may be the same or different, each has the same meaning as $R^{41}$ defined in general formula (IV); and $—C(R^{53}, R^{54})—Q'—$ has the same meaning as Q defined in general formula (I).

$R^{51}$, $R^{52}$, $R^{53}$ and $R^{54}$ each preferably represents a hydrogen atom. Further, it is preferred that at least one of Z and Q' contains a group capable of accelerating adsorption onto silver halide grains. Examples of the group capable of accelerating adsorption onto silver halide grains used include those represented by general formula (II) above.

Of the compounds represented by general formula (V), those represented by the following general formula (VI) are even more preferred.

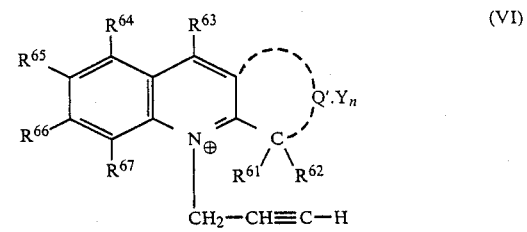

wherein Q', Y and n each has the same meaning as defined in general formula (V); $R^{61}$ and $R^{62}$ have the same meanings as $R^{53}$ and $R^{54}$ defined in the general formula (V), respectively; and $R^{63}$, $R^{64}$, $R^{65}$, $R^{66}$ and $R^{67}$ each has the same meaning as the substituent for Z defined in general formula (I).

It is preferred that at least one substituent of Q' and $R^{63}$, $R^{64}$, $R^{65}$, $R^{66}$ or $R^{67}$ contains a group capable of accelerating adsorption onto silver halide grains represented by general formula (II) above.

Specific examples of the alkynyl substituted heterocyclic quaternary ammonium salt compounds useful in the present invention are illustrated below, but the present invention should not be construed as being limited thereto:

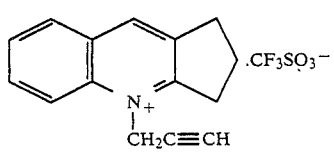 (1)
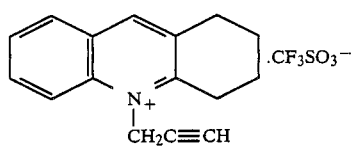 (2)
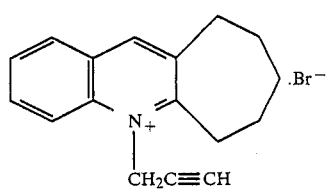 (3)
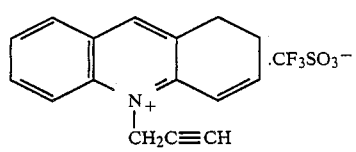 (4)
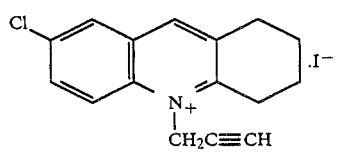 (5)
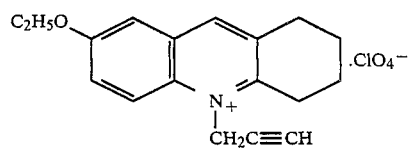 (6)
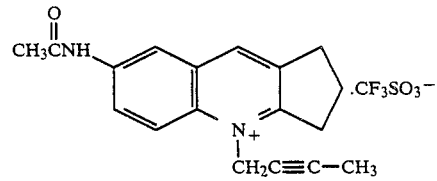 (7)
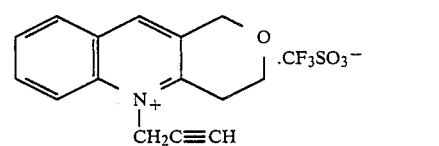 (8)
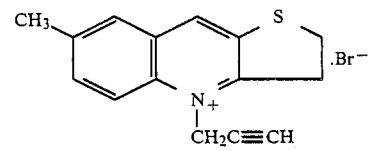 (9)

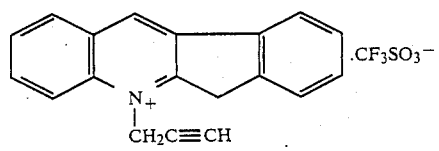 (10)
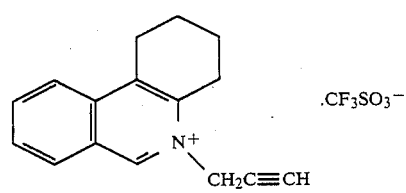 (11)
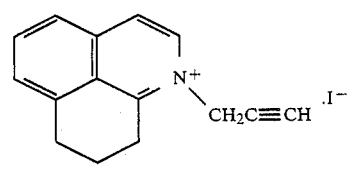 (12)
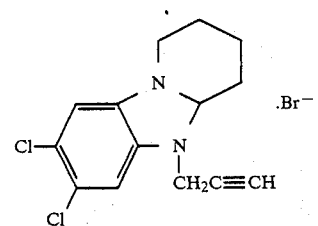 (13)
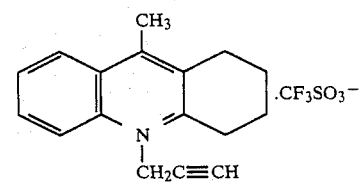 (14)
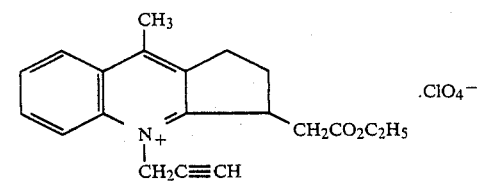 (15)
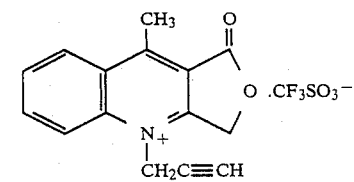 (16)
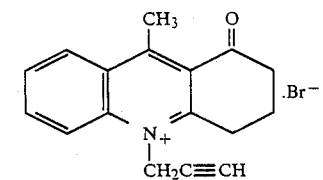 (17)

-continued
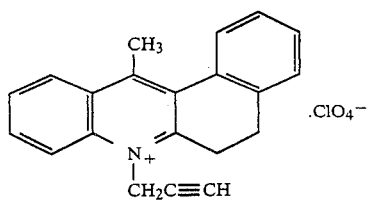 (18)
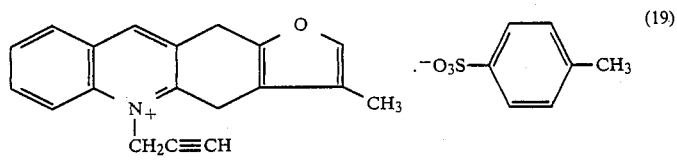 (19)
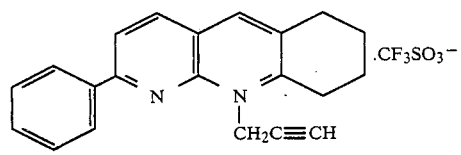 (20)
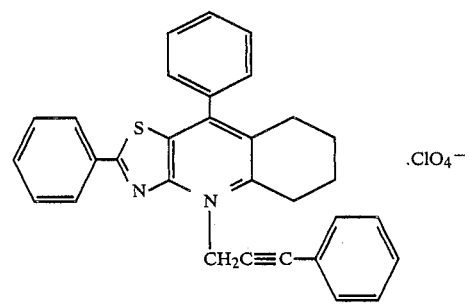 (21)
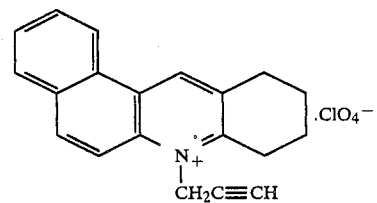 (22)
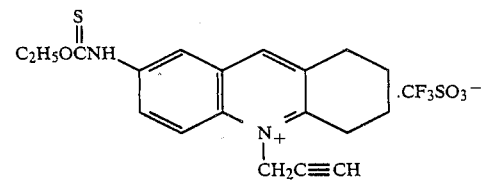 (23)
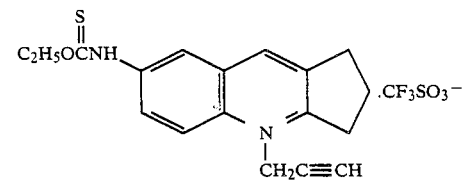 (24)

-continued
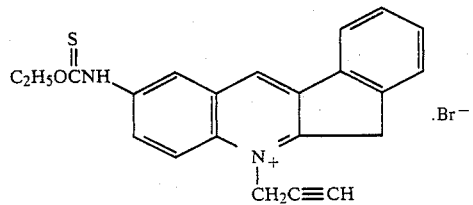 (25)
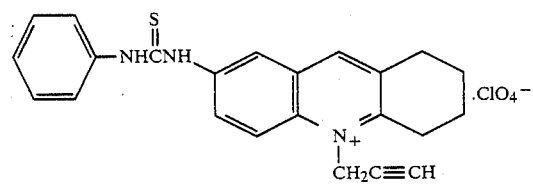 (26)
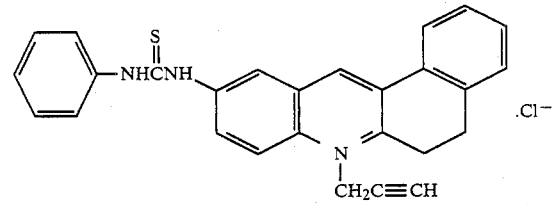 (27)
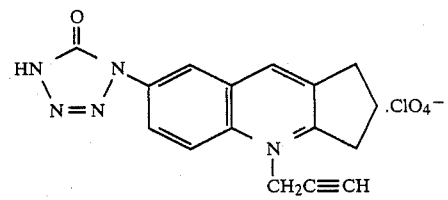 (28)
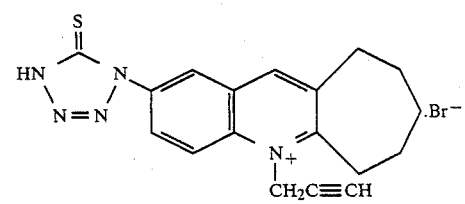 (29)
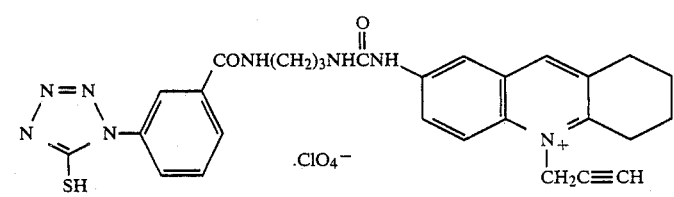 (30)
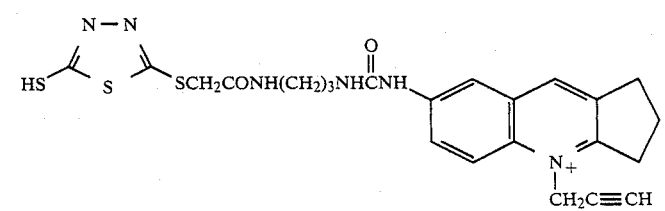 (31)

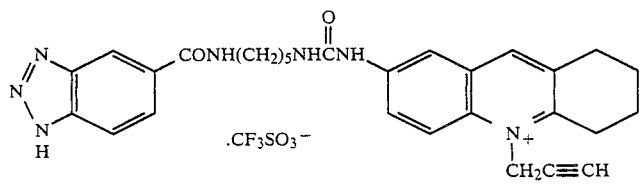 (32)
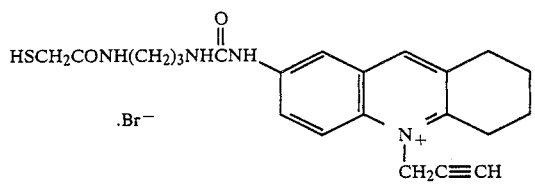 (33)
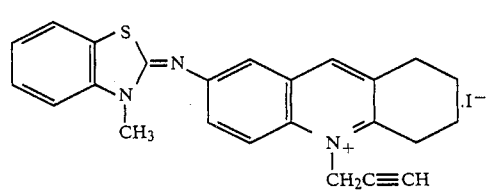 (34)
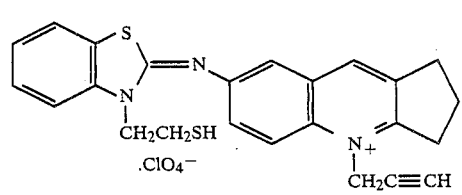 (35)
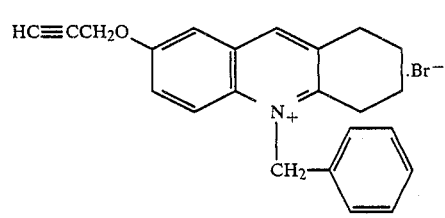 (36)
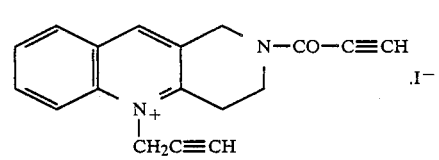 (37)
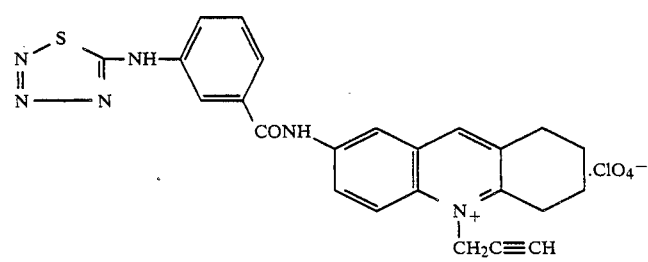 (38)
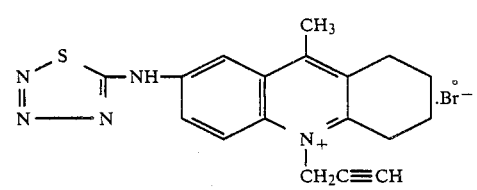 (39)

-continued
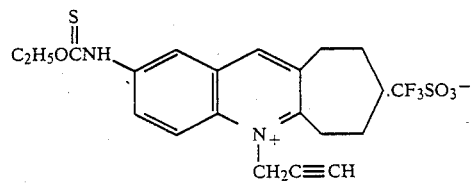
(40)
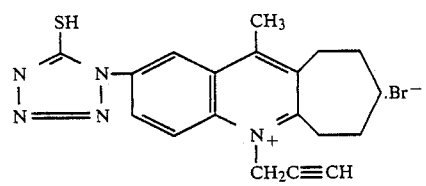
(41)
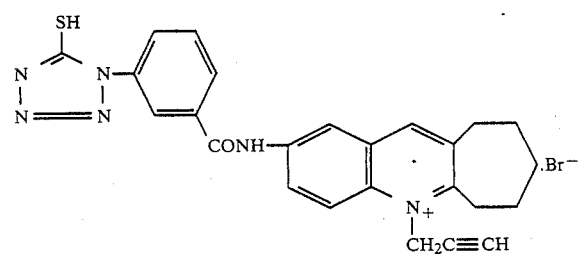
(42)
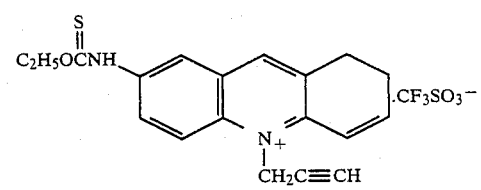
(43)
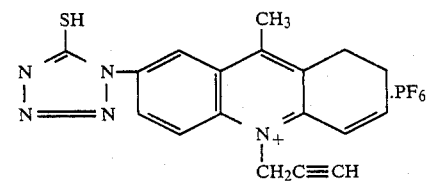
(44)
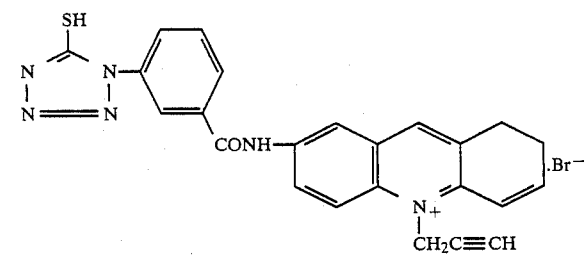
(45)
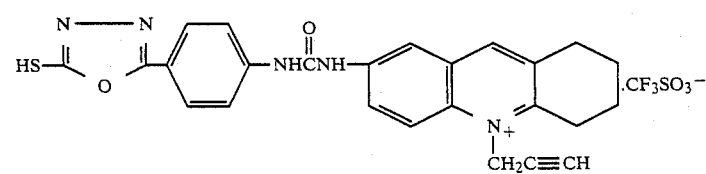
(46)
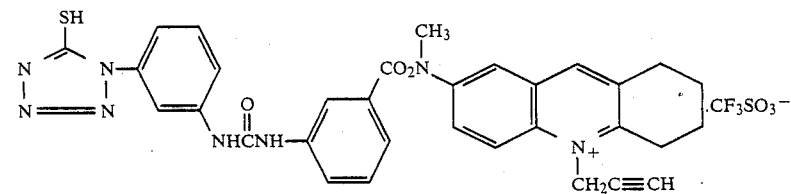
(47)

-continued
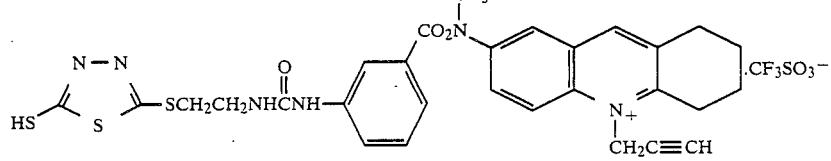
(48)
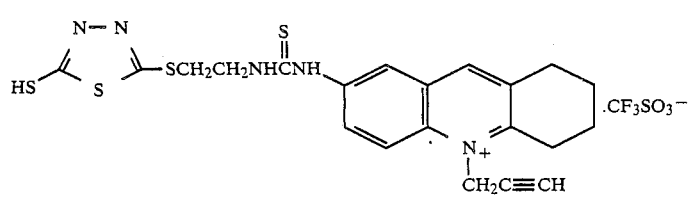
(49)
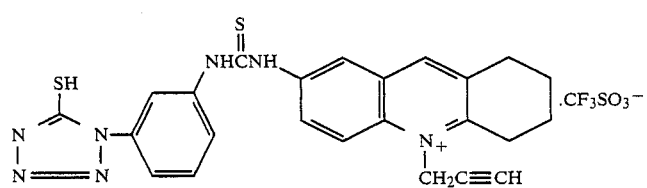
(50)
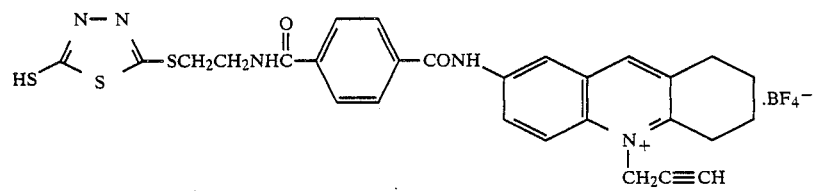
(51)
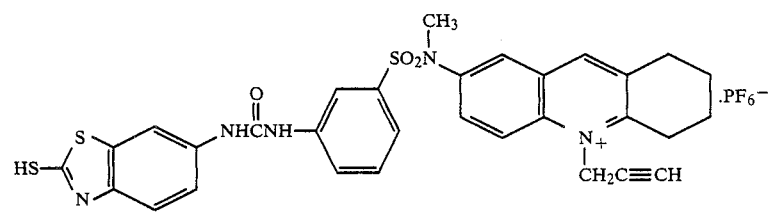
(52)
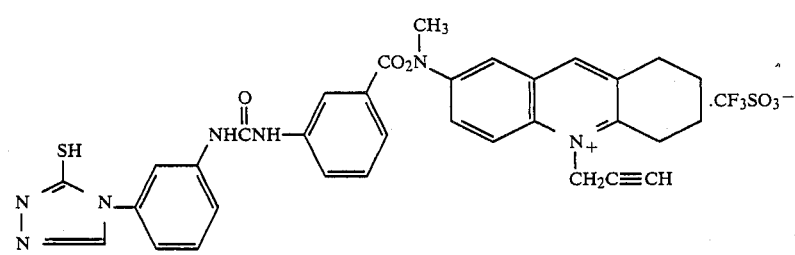
(53)
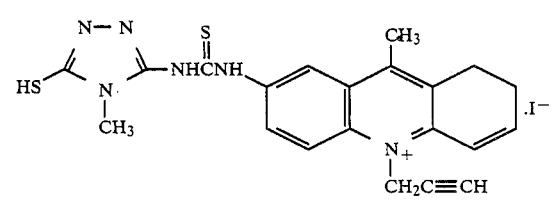
(54)
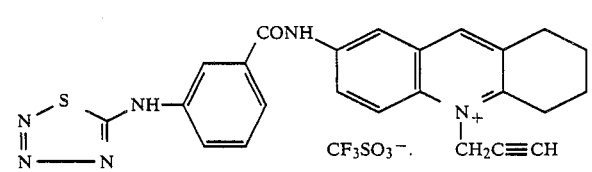
(55)

-continued
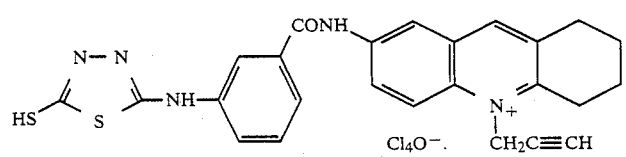
(56)
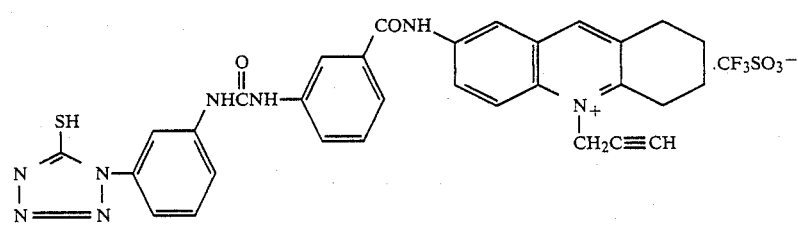
(57)
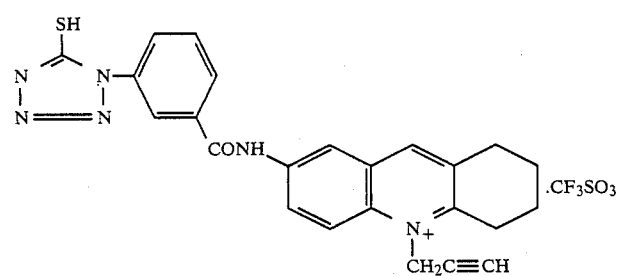
(58)
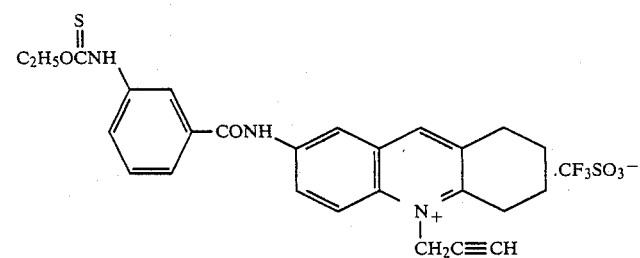
(59)
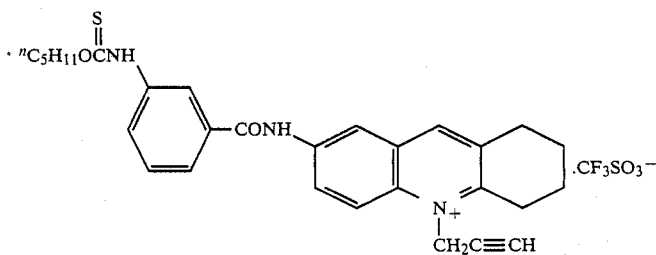
(60)
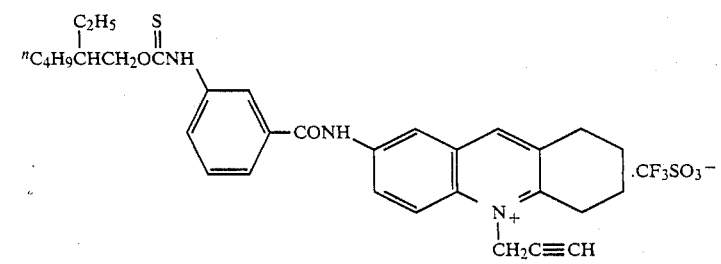
(61)

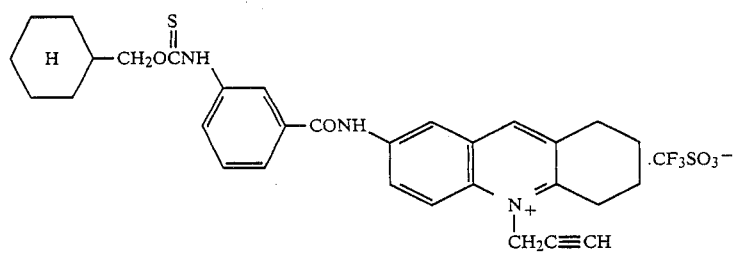
(62)
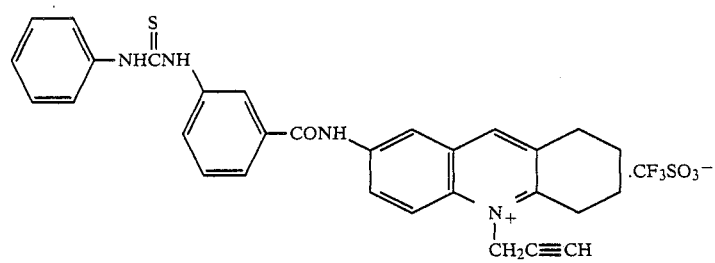
(63)
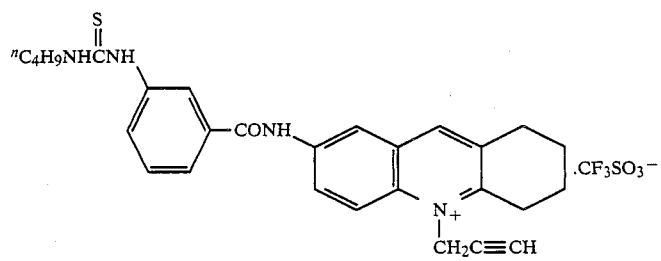
(64)
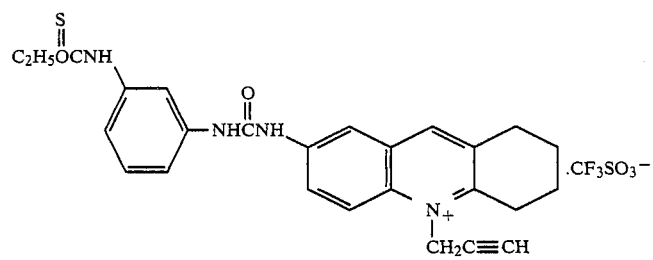
(65)
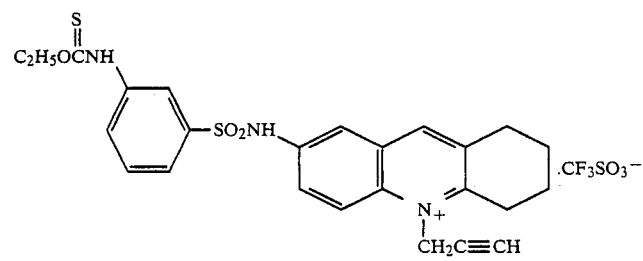
(66)
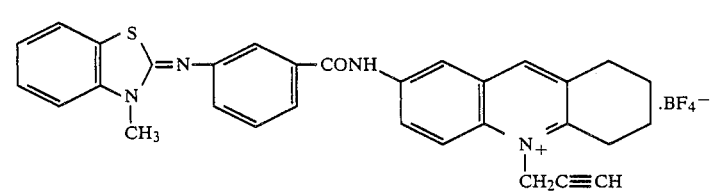
(67)

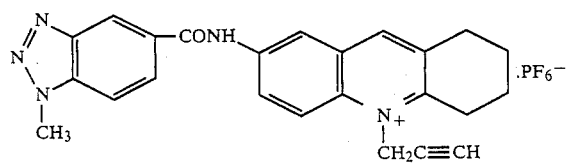

(68)

The alkynyl substituted heterocyclic quaternary ammonium salt compounds used in accordance with the present invention can be generally synthesized in the following manner.

The nitrogen-containing heterocyclic compounds

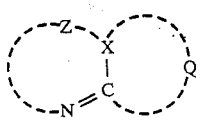

which are raw materials for the compounds represented by general formula (I) can be synthesized according to methods as described, for example, in A. R. Katrizky and C. W. Rees ed., *Comprehensive Heterocyclic Chemistry, The Structure, Reactions, Synthesis and Use of Heterocyclic Compounds*, Pergamon Press, Oxford (1984), A. Weissberger and E. C. Taylur ed., *The Chemistry of Heterocyclic Compounds*, John Willey & Sons, London (1977), C. Cheng and S. Yan, *Organic Reactions*, John Willey & Sons, New York, Vol. 28, pp. 37 (1982), etc. and methods described in the literature cited in these references.

Quaternization of the nitrogen-containing heterocyclic compound

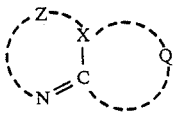

with $R^1-Y$ may be conducted by reacting these reactants in the absence of a solvent or in a solvent such as a hydrocarbon (e.g., toluene, xylene, etc.), a halogenated hydrocarbon (e.g., chloroform, carbon tetrachloride, 1,2-dichloroethane, 1,1,2,2-tetrachloroethane, etc.), or an ether (e.g., tetrahydrofuran, anisole, etc.) at a temperature of from about room temperature to about 150° C. The reaction product is recovered by adding a solvent which does not solubilize the product such as ethyl acetate or acetone, etc. to the reaction mixture, and collecting the precipitated crystals by filtration. Where crystallinity of the product is insufficient, crystallization may be satisfactorily conducted, in many cases, by base exchanging the counter ion $Y^-$ for another counter ion.

Introduction of the group represented by W capable of accelerating adsorption onto silver halide grains may be conducted by employing various linking groups L, after the quaternization of

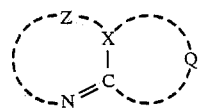

with $R^1-Y$, as illustrated below:

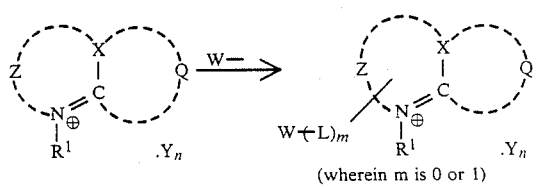

(wherein m is 0 or 1)

More specifically, synthesis methods similar to those as described, for example, in U.S. Pat. Nos. 4,471,044 and 4,115,122 can be employed. In the reaction scheme illustrated above, L represents a divalent linking group, and reaction conditions to be employed vary depending upon the type of L used in the reaction. For example, where L represents a carbonamido group, the adsorption accelerating groups W may be introduced in a conventional manner by reacting a carboxylic acid chloride or a phenyl carboxylate derivative with an amine derivative in the presence of a deoxidizer such as pyridine or triethylamine, etc. Alternatively, the group W may be introduced by reacting a carboxylic acid derivative with an amine derivative in the presence of a condensing agent such as dicyclohexylcarbodiimide, etc. Where L represents, for example, a sulfonamido group, the alkynyl substituted compound may be synthesized in a conventional manner by reacting a sulfonic acid chloride derivative with an amine derivative in the presence of a deoxidizer such as pyridine or triethylamine, etc.

Where L represents, for example, a ureido group, the alkynyl substituted compound may be synthesized by reacting an isocyanate or phenylurethane derivative with an amine derivative.

Where L represents, for example, an ether group, the alkynyl substituted compound may be synthesized by reacting an alcohol derivative with a halide derivative in the presence of an alkali such as potassium carbonate, sodium hydroxide or potassium t-butoxide, etc.

Where L represents, for example, an imino group, the compound may be synthesized in a conventional manner by reacting an amine derivative with a carbonyl derivative (an aldehyde or ketone derivative) in the presence of an acid catalyst such as hydrochloric acid or sulfuric acid, etc.

Other linking groups represented by L may also be introduced in a conventional manner.

The general methods of synthesizing the alkynyl substituted heterocyclic compounds used in accordance with the present invention are described below by reference to specific synthesis examples.

SYNTHESIS EXAMPLE 1

Synthesis of Compound (2):

To 60 ml of carbon tetrachloride containing 6 g of trifluoromethanesulfonic acid anhydride dissolved therein was added dropwise 20 ml of carbon tetrachloride containing 1.2 g of propargyl alcohol and 1.7 g of pyridine dissolved therein while maintaining the solution at −5° C. or below under cooling with a mixture of ice and methanol. The resulting mixture was further reacted for 10 minutes at room temperature, then 3 g of anhydrous sodium sulfate was added thereto and solids were removed by filtration, whereby Solution A was obtained.

Solution A was added to a mixture solution of 2.6 g of 1,2,3,4-tetrahydroacridine and 10 ml of carbon tetrachloride and the mixture was refluxed by heating for 2 hours. After the completion of the reaction, the reaction solution was stirred under cooling with ice. The crystals thus deposited were collected by filtration and recrystallized from 20 ml of ethyl acetate to obtain 2.2 g of the desired compound. Yield: 41.5%, Melting Point: 139° to 140° C.

SYNTHESIS EXAMPLE 2

Synthesis of Compound (1)

20 ml of a carbon tetrachloride solution containing 4.2 g (25 mM) of 1,2-dihydrocyclopenta[b]quinoline synthesized in a similar manner as described in *Chem. Pharm. Bull.*, Vol. 3, page 21 (1955) was added to 130 ml of a carbon tetrachloride solution containing propargyl trifluoromethanesulfonate (35.4 mM) prepared in the same manner as described in Synthesis Example 1 and the mixture was refluxed by heating for 4 hours. After the completion of the reaction, the reaction solution was stirred under cooling with ice. The crystals thus deposited were collected by filtration and recrystallized from a solvent mixture of ethyl acetate and acetonitrile (20 ml/5 ml) to obtain 2.7 g of the desired compound. Yield: 30%, Melting Point: 155° to 157° C.

SYNTHESIS EXAMPLE 3

Synthesis of Compound (4)

25 ml of a carbon tetrachloride solution containing 4.5 g (25 mM) of 1,2-dihydroacridine synthesized in a similar manner as described in the literature cited in Synthesis Example 2 was added to 130 ml of a carbon tetrachloride solution containing propargyl trifluoromethanesulfonate (35.4 mM) prepared in the same manner as described in Synthesis Example 1 and the mixture was refluxed by heating for 3 hours. After the completion of the reaction, the reaction solution was stirred under cooling with ice. The crystals thus deposited were collected by filtration and recrystallized from 30 ml of ethyl acetate to obtain 4.1 g of the desired compound. Yield: 44%, Melting Point: 146° to 147° C.

SYNTHESIS EXAMPLE 4

Synthesis of Compound (16)

30 ml of a chloroform solution containing 3.5 g (18 mM) of 2-hydroxymethyl-4-methyl-3-quinolinecarboxylic acid lactone synthesized according to the method as described in *Journal of Organic Chemistry*, Vol. 23, page 1996 (1958) was added to 96 ml of a carbon tetrachloride solution containing propargyl trifluoromethanesulfonate (26 mM) prepared in the same manner as described in Synthesis Example 1 and the mixture was refluxed by heating for 6 hours. The crystals thus deposited were collected by filtration, dissolved in 30 ml of acetonitrile and 80 ml of ethyl acetate was added thereto to recrystallize, whereby 3.8 g of the desired compound was obtained. Yield: 55%, melting Point: 185° to 187° C.

SYNTHESIS EXAMPLE 5

Synthesis of Compound (14)

In a manner similar to Synthesis Example 2, except for using 4.9 g (25 mM) of 9-methyl-1,2,3,4-tetrahydroacridine synthesized according to the method as described in *Chem. Ber.*, Vol. 97, page 16 (1964) in place of 1,2-dihydrocyclopenta[b]quinoline, 5.1 g of the desired compound was obtained. Yield: 53%, Melting Point: 164° to 165° C.

SYNTHESIS EXAMPLE 6

Synthesis of Compound (23)

25 ml of a carbon tetrachloride solution containing 6.0 g (25 mM) of 7-isothiocyanato-1,2,3,4-tetrahydroacridine synthesized in a similar manner as described in the literature cited in Synthesis Example 2 was added to 130 ml of a carbon tetrachloride solution containing propargyl trifluoromethanesulfonate (35.4 mM) prepared in the same manner as described in Synthesis Example 1 and the mixture was refluxed by heating for 3 hours. Then, 50 ml of ethanol was added thereto and the mixture was further refluxed by heating for 1 hour. The reaction mixture was cooled and the crystals thus deposited were collected by filtration and recrystallized from a solvent mixture of ethyl acetate and acetonitrile (30 ml/30 ml) to obtain 3.7 g of the desired compound. Yield: 31%, Melting Point: 213° to 214° C.

In the case of incorporating the compound represented by general formula (I) in a photographic light-sensitive material according to the present invention, it suffices to add the compound to a hydrophilic colloidal solution as a solution in a water-miscible organic solvent such as an alcohol (e.g., methanol, ethanol), an ester (e.g., ethyl acetate) or a ketone (e.g., acetone), or, where the compound is water-soluble, as an aqueous solution.

When adding the compound to a photographic emulsion, such addition may be made at any stage from the initiation of chemical ripening of the emulsion to the stage before coating the emulsion onto the element, with the stage after completion of chemical ripening being preferable as the time of addition.

In the present invention, the nucleating agent represented by general formula (I) may be incorporated in at least one hydrophilic colloidal layer adjacent to a silver halide emulsion layer, but is preferably incorporated in at least one silver halide emulsion layer. The amount of the nucleating agent to be added can vary over a wide range since it varies depending upon the properties of silver halide emulsion which is actually used, the chemical structure of the nucleating agent, and the developing conditions. However, the nucleating agent represented by formula (I) is generally added in an amount of from about $1 \times 10^{-8}$ mol to about $1 \times 10^{-2}$ mol per mol of silver in each silver halide emulsion layer to which the nucleating agent is added, preferably from $1 \times 10^{-7}$ mol to $1 \times 10^{-3}$ mol per mol of silver in each silver halide emulsion layer to which the nucleating agent is added.

With negative emulsions, the nucleating agent is added preferably in an amount of from about $1 \times 10^{-5}$ mol to about $1 \times 10^{-3}$ mol per mol of silver in the silver halide emulsion.

The internal latent image type silver halide emulsion not having been previously fogged which can be used in the present invention includes an emulsion containing silver halide grains whose surfaces have not been previously fogged, and which form latent images predominantly internally. More specifically, suitable emulsions have the characteristic that when coated on a transparent support in a predetermined amount ranging from about 0.5 g/m² to about 3 g/m² in terms of silver, exposed for a fixed time between about 0.01 and about 10 seconds, then developed at about 18° C. for about 5 minutes in the following developing solution A (an internal developer), such emulsions provide images having a maximum density (measured by a conventional photographic density measuring method) of at least about 5 times, more preferably at least about 10 times, as much as that obtained by coating and exposing the emulsion in the same manner as described above, but developing at 20° C. for 6 minutes in the following developing solution B (surface developer):

| Internal developer A | |
|---|---|
| Metol | 2 g |
| Sodium sulfite (anhydrous) | 90 g |
| Hydroquinone | 8 g |
| Sodium carbonate (monohydrate) | 52.5 g |
| KBr | 5 g |
| KI | 0.5 g |
| Water to make | 1 liter |
| Surface developer B | |
| Metol | 2.5 g |
| l-Ascorbic acid | 10 g |
| $NaBO_2.H_2O$ | 35 g |
| KBr | 1 g |
| Water to make | 1 liter |

Specific examples of the internal latent image type emulsions include conversion type silver halide emulsions and emulsions having shells over a core of such conversion type silver halide emulsions as described, for example, in U.S. Pat. No. 2,592,250, Japanese Patent Publication Nos. 54379/83, 3536/83 and 5582/85, Japanese Patent Application (OPI) Nos. 156614/77, 79940/82 and 70221/83, etc.; and core/shell type silver halide emulsions the core of which is doped with a metal as described, for example, in U.S. Pat. Nos. 3,761,276, 3,850,637, 3,923,513, 4,035,185, 4,395,478, 4,431,730 and 4,504,570, Japanese Patent Application (OPI) Nos. 60222/78, 22681/81, 208540/84, 107641/85 and 3137/86, and the patents cited in *Research Disclosure*, No. 23510 (November, 1983), p. 236, page 236, ibid., No. 18155 (May, 1979), pages 265 to 268, etc.

The silver halide grains used in the present invention may be regularly-shaped crystals such as cubic, octahedral, dodecahedral or tetradecahedral crystals, or may be irregularly-shaped crystals such as spherical crystals or tabular grains whose length/thickness ratio is about 5 or more. A composite form of these crystal forms may be used, and an emulsion made up of a mixture of these crystals may also be used.

The composition of the silver halide includes silver chloride, silver bromide or a mixture of silver halides, and the silver halide preferably used in the present invention is either free from silver iodide, or if it contains a silver iodide, it is in the form of silver chloro(iodo)bromide, silver (iodo)chloride or silver (iodo)bromide containing about 3 mol % or less of silver iodide.

The average grain size of the silver halide grains is preferably up to about 2 μm from about 0.1 μm, more preferably from 0.15 μm to 1 μm. Although the distribution of the grain size may be wide or narrow, in order to improve graininess, sharpness, etc., it is preferred in the present invention to use a so-called "monodispersed" silver halide emulsion having a narrow grain size distribution such that about 95% or more of all the grains fall within about ±40%, preferably ±20%, of the average grain size, in terms of grain number or weight.

In order to satisfy the gradation required for the photographic light-sensitive material of the present invention, in emulsion layers having substantially the same color sensitivity, two or more monodispersed silver halide emulsions different in grain size or a plurality of grains of the same size but separate in sensitivity are mixed in the same layer or are applied as different layers that are superposed, one on the other. Two or more polydispersed silver halide emulsions or a monodispersed silver halide emulsion and a polydispersed silver halide emulsion can be used in the form of a mixture or in superposed layers to achieve the desired gradation.

In the silver halide emulsion used in the present invention, the interior or the surface of the grains may be chemically sensitized by sulfur sensitization, selenium sensitization, reduction sensitization or noble metal sensitization, which may be used alone or in combination. Specific examples of useful chemical sensitization methods are described, for example, in the patents cited in *Research Disclosure*, No. 17643-III (December, 1978), page 23, etc.

The photographic emulsion used in the present invention is usually spectrally sensitized with a photographic sensitizing dye in a conventional manner. Particularly useful dyes are cyanine dyes, merocyanine dyes and complex merocyanine dyes, which may be used alone or in combination, and also can be used in combination with supersensitizers. Specific examples of these dyes are described, for example, in the patents cited in *Research Disclosure*, No. 17643-IV (December, 1978), pages 23 to 24.

The photographic emulsions used in the present invention can contain an antifoggant or a stabilizer for the purpose of stabilizing the photographic characteristics, or of preventing formation of fog during the production, storage or photographic processing of the photographic light-sensitive material. Specific examples of antifoggants and stabilizers are described, for example, in *Research disclosure*, No. 17643-VI (December, 1978), pages 24 to 25, and E. J. Birr, *Stabilization of Photographic Silver Halide Emulsion*, 1974 (Focal Press), etc.

In order to form direct positive color images, various color couplers can be employed. Useful color couplers are compounds that can couple with an oxidation product of an aromatic primary amine type color developing agent to produce or release a dye, preferably a substantially non-diffusible dye and the coupler itself also being substantially non-diffusible. Typical examples of useful color couplers include naphtholic or phenolic compounds, pyrazolone or pyrazoloazole compounds and open chain or heterocyclic ketomethylene compounds. Specific examples of these cyan, magenta and yellow couplers include the compounds described in *Research Disclosure*, No. 17643 (December, 1978), page 25, section VII-D; ibid., No. 18717 (November, 1979); Japanese Patent Application (OPI) No. 215272/87 (pages 298 to 373); and compounds described in the patents cited in these references.

Among others, typical yellow couplers that can be used in the present invention include yellow two-equivalent couplers of the oxygen atom releasing or nitrogen atom releasing type. Particularly, α-pivaloylacetanilide type couplers are excellent in fastness, in particular light-fastness, of the dyes formed therefrom, while α-benzoylacetanilide type couplers are preferred because a high color density can be obtained.

5-Pyrazolone type magenta couplers preferably used in the present invention are 5-pyrazolone type couplers (particularly, sulfur atom releasing type two-equivalent couplers), substituted at the 3-position with an arylamino group or an acylamino group.

Pyrazoloazole type couplers are further preferred. Among them, pyrazolo[5,1-c][1,2,4]triazoles as described in U.S. Pat. No. 3,725,067 are preferred, imidazo[1,2-b]pyrazoles as described in U.S. Pat. No. 4,500,630 are more preferred in view of the fastness to light and the low yellow subsidiary absorption of the dye formed therefrom, and pyrazolo[1,5-b][1,2,4]triazoles as described in U.S. Pat. No. 4,540,654 are most preferred.

Cyan couplers preferably used in the present invention include naphtholic and phenolic couplers as described in U.S. Pat. Nos. 2,474,293 and 4,052,212, etc. and phenolic cyan couplers having an alkyl group containing two or more carbon atoms at the m-position of the phenol nucleus as described in U.S. Pat. No. 3,772,002. In addition, 2,5-diacylamino-substituted phenolic couplers are also preferred in view of fastness of color image formed.

Specific examples of particularly preferred yellow, magenta and cyan couplers are compounds listed in Japanese Patent Application No. 169523/86 (corresponding to U.S. Pat. Application Serial No. 075,008), pages 35 to 51, and the compounds illustrated below are also preferred examples.

Magenta Coupler

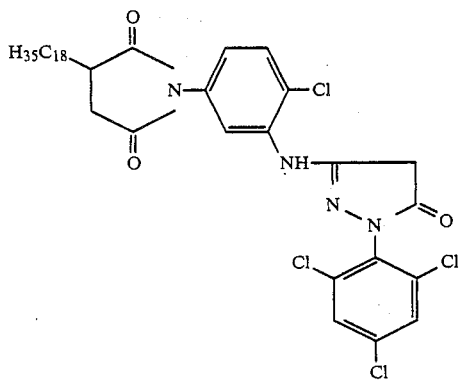

(M-12)

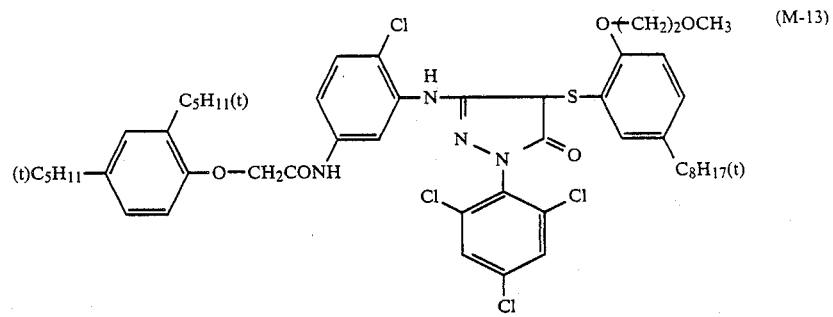

(M-13)

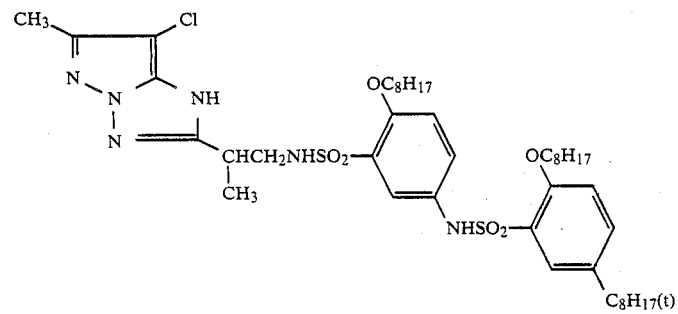

(M-14)

(M-15)
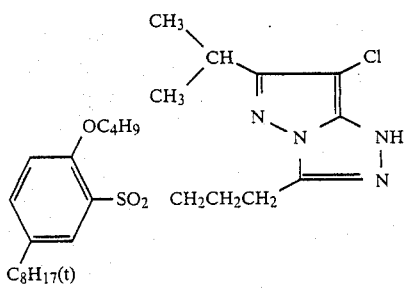
Yellow Coupler
(Y-9)
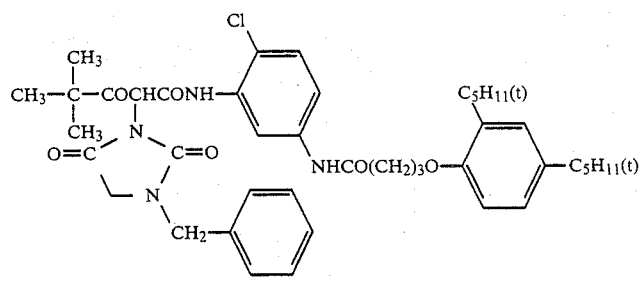
(Y-10)
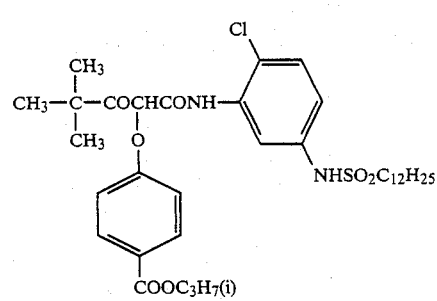
(Y-11)
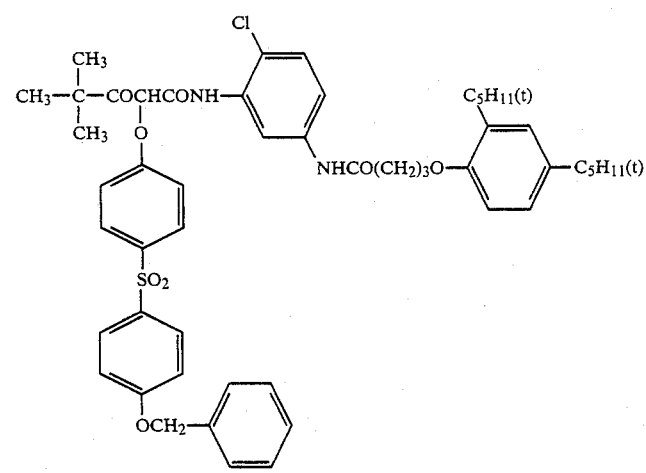
Cyan Coupler
(C-10)
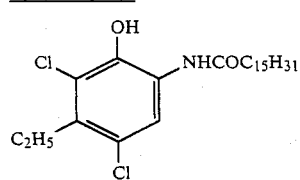

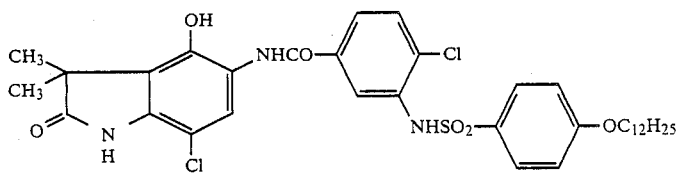

(C-11)

Colored couplers for correcting undesired absorption in the short wavelength range of produced dyes, couplers capable of forming dyes with appropriate diffusibility, non-color forming couplers, DIR couplers capable of releasing a development inhibitor as a result of the coupling reaction, couplers that can release a development accelerator, and polymerized couplers can also be used as is conventional in this art.

Generally, the amount of a color coupler used is in the range of about 0.001 to about 1 mol per mol of a light-sensitive silver halide, and preferably in the case of a yellow coupler the amount is about 0.01 to about 0.5 mol per mol of a light-sensitive silver halide, in the case of a magenta coupler the amount is about 0.03 to about 0.5 mol per mol of a light-sensitive silver halide, and in the case of a cyan coupler the amount is about 0.002 to about 0.5 mol per mol of a light-sensitive silver halide.

The photographic light-sensitive material in accordance with the present invention may contain, as a color fog preventing agent or color mixing preventing agent, hydroquinone derivatives, aminophenol derivatives, amines, gallic acid derivatives, catechol derivatives, ascorbic acid derivatives, non-color forming couplers, sulfonamidephenol derivatives, etc. Typical examples of color fog preventing agents and color mixing preventing agent are described in Japanese Patent Application (OPI) No. 215272/87, pages 600 to 630.

In the photographic light-sensitive material of the present invention, various color fading preventing agents can be used. Typical organic color fading preventing preventing agents include hydroquinones, 6-hydroxychromans, 5-hydroxycoumarans, spirochromans, p-alkoxyphenols, hindered phenols including bisphenols, gallic acid derivatives, methylenedioxybenzenes, aminophenols, hindered amines and ether or ester derivatives obtained by the silylation or alkylation of the phenolic hydroxyl group of these compounds. Further, metal complexes such as (bissalicylalkoxymato)-nickel complex and (bis-N,N-dialkyldithiocarbamato)-nickel complexes can be used for this purpose.

For the purpose of preventing yellow dye images from being deteriorated by heat, humidity and light, compounds having both a hindered amine and a hindered phenol in a single molecule, as described in U.S. Pat. No. 4,268,593, give good results. For the purpose of preventing magenta dye images from being deteriorated, particularly by heat, spiroindanes as described in Japanese Patent Application (OPI) No. 159644/81 and chromans substituted with hydroquinone diethers or monoethers as described in Japanese Patent Application (OPI) No. 89835/80 give good results.

Typical examples of these color fading preventing agents are described in Japanese Patent Application (OPI) No. 215272/87, pages 401 to 440. The desired aim can be attained when these compounds are added to light-sensitive layers generally in amounts of about 5 to about 100 wt % based on the respective color couplers by co-emulsifying them with the couplers.

For the purpose of preventing cyan dye images from being deteriorated by heat and, particularly, from being deteriorated by light, it is effective to introduce an ultraviolet ray absorbing agent into both layers adjacent to a cyan color forming layer. An ultraviolet ray absorbing agent can also be added to a hydrophilic colloid layer such as protective layer. Typical examples of such compounds are described in Japanese Patent Application (OPI) No. 215272/87, pages 391 to 400.

As binders or protective colloids which can be used in emulsion layers and other hydrophilic colloid-containing intermediate layers of the light-sensitive material of the present invention, it is advantageous to use gelatin, but other hydrophilic colloids other than gelatin can also be used.

The light-sensitive material of the present invention can contain dyes for preventing irradiation or halation, ultraviolet ray absorbing agents, plasticizers, fluorescent brightening agents, matting agents, aerial fog preventing agents, coating aids, hardening agents, antistatic agents, lubricants, etc. Typical examples of these additives are described in Research Disclosure, No. 17643, sections VIII to XIII (December, 1978), pages 25 to 27, and ibid., No. 18716 (November, 1979), pages 647 to 651.

The present invention can be applied to multilayer multicolor photographic materials having at least two layers having different spectral sensitivities on a support. Generally a multilayer natural color photographic material has at least one red-sensitive emulsion layer, at least one green-sensitive emulsion layer and at least one blue-sensitive emulsion layer on a support. The order of these layers is appropriately selected as desired by one of ordinary skill in the art. In a preferred order of the layers, a red-sensitive emulsion layer, a green-sensitive emulsion layer and a blue-sensitive emulsion layer are coated in that order on a support, or a green-sensitive emulsion layer, a red-sensitive emulsion layer and a blue-sensitive emulsion layer are coated in that order on a support. Each of these emulsion layers may comprise of two or more emulsion layers having differing sensitivities, or may comprise two or more emulsion layers having the same sensitivity with a light-insensitive layer between them. Generally, the red-sensitive emulsion layer contains a cyan forming coupler, the green-sensitive emulsion layer contains a magenta forming coupler and the blue-sensitive emulsion layer contains a yellow forming coupler, but in some cases the combination can be changed.

It is preferred that the light-sensitive material according to the invention is provided with suitable auxiliary layers such as a protective layer, an intermediate layer, a filter layer, an antihalation layer, a backing layer and a white reflective layer, in addition to the silver halide emulsion layers.

In the photographic light-sensitive materials of the present invention, the photographic emulsion layers and other layers are applied on supports, such as those described in *Research Disclosure*, No. 17643, section XVII (December, 1978), page 28, European Patent No. 0,182,253, and Japanese Patent Application (OPI) No. 97655/86. The coating methods as described in *Research Disclosure*, No. 17643, section XV, pages 28 to 29 can be conveniently employed.

When using the photographic light-sensitive material of the present invention for a color diffusion transfer process, coloring materials which themselves are non-diffusible (immobile) in an alkaline solution (developer) but, as a result of development, release a diffusible dye (or its precursor) are advantageously used, while dye developers may be employed as coloring materials. Suitable diffusible dye-releasing type coloring materials (DRR compounds) include couplers and redox compounds capable of releasing a diffusible dye. These are useful not only for color diffusion transfer processes (wet processes), but also for thermally developing processes (dry processes) as described, for example, in Japanese Patent Application (OPI) No. 58543/83.

The diffusible dye-releasing redox compounds (hereinafter referred to as "DRR compounds") can be represented by the following general formula:

(Ballast)—(Redox-cleavable atomic group)—D

In the above formula, Ballast and Redox-cleavable atomic group may be those compounds which are described in Japanese Patent Application (OPI) No. 163938/83, pages 12 to 22. D represents a dye (or its precursor) moiety. This dye or dye precursor moiety may be bound to the Redox-cleavable atomic group through a linking group. As the dye moiety represented by D, those which are described in the following literature references are effective:

Examples of yellow dyes:

Those which are described in U.S. Pat. Nos. 3,597,200, 3,309,199, 4,013,633, 4,245,028, 4,156,609, 4,139,383, 4,195,992, 4,145,641, 4,148,643 and 4,336,322, Japanese Patent Application (OPI) Nos. 114930/76 and 71072/81, *Research Disclosure*, No. 17630 (1978) and ibid., No. 16475 (1977), etc.

Examples of magenta dyes:

Those which are described in U.S. Pat. Nos. 3,435,107, 3,544,545, 3,932,380, 3,931,144, 3,932,308, 3,954,476, 4,233,237, 4,255,509, 4,250,246, 4,142,891, 4,207,104 and 4,287,292, Japanese Patent Application (OPI) Nos. 106727/77, 23628/78, 36804/80, 73057/81, 71060/81, and 134/80, etc.

Examples of cyan dyes:

Those which are described in U.S. Pat. Nos. 3,482,972, 3,929,760, 4,013,635, 4,268,625, 4,171,220, 4,242,435, 4,142,891, 4,195,994, 4,147,544 and 4,148,642, British Patent 1,551,138, Japanese Patent Application (OPI) Nos. 99431/79, 8827/77, 47823/78, 143323/78, 99431/79, 71061/81, European Patents 53,037 and 53,040, *Research Disclosure*, No. 17630 (1978) and ibid., No. 16475 (1977), etc.

These compounds are suitably coated in amounts of from about $1 \times 10^{-4}$ to about $1 \times 10^{-1}$ mol/m$^2$, preferably from $2 \times 10^{-4}$ to $2 \times 10^{-2}$ mol/m$^2$.

In the present invention, these DRR type coloring materials may be incorporated in the silver halide emulsion layer associated with them, or in an adjacent layer to the emulsion layer on the exposure side or on the opposite side.

In the case of using the photographic light-sensitive material of the present invention for a color diffusion transfer process, the photographic emulsions may be coated on the same support as image-receiving layers, or may be coated on different supports. The silver halide photographic emulsion layers (light-sensitive element) and the image-receiving layers (image-receiving element) may be provided in a combined form as a film unit, or may be provided as separate and independent photographic materials. As the form of such a film unit, those which are kept together throughout the steps of exposure, development, transfer, and viewing the diffused image obtained or those which are peeled apart after development may be employed, with the latter type being more effective in accordance with the present invention.

Further, the present invention may be applied to various other types of color light-sensitive materials.

For instance, color reversal films for slides and television, color reversal papers, instant color films, etc. are typical examples. In addition, the present invention may be applied to color hard copies for preserving images of full color copiers or CRT. The present invention is also applicable to black-and-white light-sensitive materials utilizing mixing of three color couplers, as described in *Research Disclosure*, No. 17123 (July, 1978), etc.

The light-sensitive material of the present invention can form direct positive color images by imagewise exposing it to light, then by subjecting the exposed material to development with a surface developer containing an aromatic primary amine color developing agent in the presence of a nucleating agent, followed by bleaching and fixing.

For the purposes of increasing maximum image density, reducing minimum image density, improving preservability of the light-sensitive material, and quickening the development process, and for other purposes, the following compounds can be added to the photographic material: hydroquinones (e.g., compounds as described in U.S. Pat. Nos. 3,227,552 and 4,279,987); chromans (e.g., compounds as described in U.S. Pat. No. 4,268,621, Japanese Patent Application (OPI) No. 103031/79, and *Research Disclosure*, No. 18264 (June, 1979), pages 333 to 334); quinones (e.g., compounds as described in *Research Disclosure*, No. 21206 (December, 1981), pages 433 to 434); amines (e.g., compounds as described in U.S. Pat. No. 4,150,993 and Japanese Patent Application (OPI) No. 174757/83); oxidizing agents (e.g., compounds as described in Japanese Patent Application (OPI) No. 260039/85 and *Research Disclosure*, No. 16936 (May, 1978), pages 10 to 11); catechols (e.g., compounds as described in Japanese Patent Application (OPI) Nos. 21013/80 and 65944/80), compounds capable or releasing a nucleating agent at the time of development (e.g., compounds as described in Japanese Patent Application (OPI) No. 107029/85), thioureas (e.g., compounds as described in Japanese Patent Application (OPI) No. 95533/85); and spirobisindanes (e.g., compounds as described in Japanese Patent Application (OPI) No. 65944/80).

Nucleation accelerating agents which can be used in the present invention include pentaazaindenes, triazaindenes and tetraazaindenes having at least one mercapto group that may be optionally substituted with an alkali metal atom or an ammonium group, and compounds as described in Japanese Patent Application Nos.

136949/86 (pages 12 to 43) corresponding to U.S. Patent Application Serial No. 060,790, pages 9 to 39, and 153481/86 (pages 10 to 29) corresponding to U.S. Patent Application Serial No. 067,850, pages 9 to 29.

Specific examples of the nucleation accelerating agents are illustrated below, but the present invention is not to be construed as being limited to those compounds:

(A-1): 3-mercapto-1,2,4-triazolo[4,5-a]pyridine
(A-2): 3-mercapto-1,2,4-triazolo[4,5-a]pyrimidine
(A-3): 5-mercapto-1,2,4-triazolo[1,5-a]pyrimidine
(A-4): 7-(2-dimethylaminoethyl)-5-mercapto-1,2,4-triazolo[1,5-a]pyrimidine
(A-5): 3-mercapto-7-methyl-1,2,4-triazolo[4,5-a]pyrimidine
(A-6): 3,6-dimercapto-1,2,4-triazolo[4,5-b]pyridadine
(A-7): 2-mercapto-5-methylthio-1,3,4-thiadiazole
(A-8): 3-mercapto-4-methyl-1,2,4-triazole
(A-9): 2-(3-dimethylaminopropylthio)-5-mercapto-1,3,4-thiadiazole hydrochloride
(A-10): 2-(2-morpholinoethylthio)-5-mercapto-1,3,4-thiadiazole hydrochloride
(A-11): 2-mercapto-5-methylthiomethylthio-1,3,4-thiadiazole sodium salt
(A-12): 4-(2-morpholinoethyl)-3-mercapto-1,2,4-triazole
(A-13): 2-[2-(2-dimethylaminoethylthio)ethylthio]-5-mercapto-1,3,4-thiadiazole hydrochloride It is preferred that the nucleation accelerating agent is added to a silver halide emulsion or a layer adjacent thereto.

The amount of the nucleation accelerating agent added to the material is preferably from about $10^{-6}$ to about $10^{-2}$ mol, more preferably from $10^{-5}$ to $10^{-2}$ mol, per mol of a silver halide in the emulsion layer or adjacent layer.

If the nucleation accelerating agent is added to a processing solution, i.e., a developing solution or a bath prior to the developing solution, the amount of the nucleation accelerating agent is from about $10^{-8}$ to about $10^{-3}$ mol, preferably from $10^{-7}$ to $10^{-4}$ mol, per liter of the processing solution, if desired.

Two or more nucleation accelerating agents can be used in combination, if desired.

The color developing solution used for development processing of the light-sensitive material of the present invention substantially excludes a silver halide solvent and is preferably an alkaline solution whose major component is an aromatic primary amine color developing agent. As the color developing agent, while aminophenol type compounds are useful, p-phenylenediamine type compounds are preferred. Typical examples thereof are 3-methyl-4-amino-N-ethyl-N-(β-methanesulfonamidoethyl)aniline, 3-methyl-4-amino-N-ethyl-N-(β-hydroxyethyl)aniline and 3-methyl-4-amino-N-ethyl-N-methoxyethylaniline and their sulfates and hydrochlorides, etc. As the color developing agents, compounds as described by L. F. A. Mason in Photographic Processing Chemistry, pages 226 to 229 (Focal Press, 1966), U.S. Pat. Nos. 2,193,015 and 2,592,364, and Japanese Patent Application (OPI) No. 64933/73, etc. can also be used. If desired, two or more color developing agents can be used in combination.

The amount of the color developing agent used is preferably from about 0.1 to 20 g, more preferably from 0.5 to 15 g, per liter of the developing solution.

The developing solution can further contain preservatives including, for example, aromatic polyhydroxy compounds as described, for example, in Japanese Patent Application (OPI) Nos. 49828/77, 47038/81, 32140/81 and 160142/84 and U.S. Pat. No. 3,746,544; hydroxyacetones as described, for example, in U.S. Pat. No. 3,615,503 and British Patent 1,306,176; α-aminocarbonyl compounds as described, for example, in Japanese Patent Application (OPI) Nos. 143020/77 and 89425/78; various metals as described, for example, in Japanese Patent Application (OPI) Nos. 44148/82 and 53749/82; saccharides as described, for example, in Japanese Patent Application (OPI) No. 102727/77; hydroxamic acids as described, for example, in Japanese Patent Application (OPI) No. 27638/77; α,α'-dicarbonyl compounds as described, for example, in Japanese Patent Application (OPI) No. 160141/84; salicylic acids as described, for example, in Japanese Patent Application (OPI) No. 180588/84; alkanolamines as described, for example, in Japanese Patent Application (OPI) No. 3532/79; poly(alkyleneimines) as described, for example, in Japanese Patent Application (OPI) No. 94349/81; and gluconic acid derivatives as described, for example, in Japanese Patent Application (OPI) No. 75647/81; etc. These preservatives may be used in combination of two or more if desired. Particularly, the addition of 4,5-dihydroxy-m-benzenedisulfonic acid, poly(ethyleneimine) and triethanolamine is preferred. The addition of substituted phenols such as p-nitrophenol is also preferred. The use of alkylhydroxylamine compounds as described in Japanese Patent Application (OPI) No. 3532/79 is also preferred. Particularly, it is preferred that alkylhydroxylamine compounds be used in combination with the above-described preservatives.

The amount of the preservatives to be used is preferably from about 0.1 to about 20 g, more preferably from 0.5 to 10 g, per liter of the developing solution.

The pH of the color developing solution used in the present invention is preferably not more than about 11.5, more preferably from 9.5 to 11.2, and particularly preferably from 9.8 to 11.0. In order to maintain this pH range, various buffers can be used. Suitable examples of buffers include carbonates such as potassium carbonate, phosphates such as potassium phosphate and compounds as described in Japanese Patent Application (OPI) No. 215272/87, pages 11 to 22.

The color developing solution can further contain various chelating agents as agents for preventing calcium and magnesium from precipitating or for improving the stability of the color developing solution.

Suitable chelating agents include, for example, aminopolycarboxylic acids as described in Japanese Patent Publication Nos. 30496/73 and 30232/69; organic phosphonic acids as described in Japanese Patent Application (OPI) No. 97347/81, Japanese Patent Publication No. 39359/81 and West German Patent 2,227,639; phosphonocarboxylic acids as described in Japanese Patent Application (OPI) Nos. 102726/77, 42730/78, 121127/79, 126241/80 and 65956/80; and other compounds as described in Japanese Patent Application (OPI) Nos. 195845/83 and 203440/83 and Japanese Patent Publication No. 40900/78; etc. These chelating agents may be used in combination of two or more if required. The amount of the chelating agents to be added is that amount which is sufficient to form complexes with metal ions present in the color developing solution. For example, the amount is on the order of about 0.1 to about 10 g per liter.

If desired, any conventional development accelerator can be added to the color developing solution.

Suitable development accelerators include thioether type compounds as described, for example, in Japanese Patent Publication Nos. 16088/62, 5987/62, 7826/63, 12380/69 and 9019/70, and U.S. Pat. No. 3,813,247, etc.; p-phenylenediamine type compounds as described, for example, in Japanese Patent Application (OPI) Nos. 49828/77 and 15554/75, etc.; quaternary ammonium salts as described, for example, in Japanese Patent Application (OPI) No. 137726/75, Japanese Patent Publication No. 30074/69 and Japanese Patent Application (OPI) Nos. 156826/81 and 43429/77, etc; p-aminophenols as described, for example, in U.S. Pat. Nos. 2,610,122 and 4,119,462, etc.; amine type compounds as described, for example, in U.S. Pat. Nos. 2,494,903, 3,128,182, 4,230,796 and 3,253,919, Japanese Patent Publication No. 11431/66, U.S. Pat. Nos. 2,482,546, 2,596,926 and 3,582,346, etc.; polyalkylene oxides as described, for example, in Japanese Patent Publication Nos. 16088/62 and 25201/67, U.S. Pat. No. 3,128,183, Japanese Patent Publication Nos. 11431/66 and 23883/67 and U.S. Pat. No. 3,532,501; and further 1-phenyl-3-pyrazolidones, hydrazines, meso-ionic compounds, thione compounds, imidazoles, etc. Particularly, thioether type compounds and 1-phenyl-3-pyrazolidones are preferred.

If desired, any conventional antifoggant can be added to the color developing solution used in the present invention. Suitable antifoggants include an alkali metal halide such as potassium bromide, sodium chloride and potassium iodide or an organic antifoggant. Suitable organic antifoggants include, for example, a nitrogen-containing heterocyclic compound such as benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole and hydroxyazaindolizine; a mercapto-substituted heterocyclic compound such as 2-mercaptobenzimidazole and 2-mercaptobenzothiazole; and a mercapto-substituted aromatic compound such as thiosalicyclic acid and adenine. Although these antifoggants may dissolve out of the color light-sensitive material during processing and may accumulate in the color developing solution, it is preferred that the amount of such accumulation be limited to reduce the discharge amount thereof in the developing solution.

It is preferred that the color developing solution used in the present invention contain a fluorescent brightening agent. It is preferred to use, as a fluorescent brightening agent, a 4,4-diamino-2,2'-disulfostilbene type compound. The amount of the fluorescent brightening agent to be added is from 0 to about 5 g/liter, preferably from 0.1 to 2 g/liter.

If desired, various surface active agents may be added, such as alkylphosphonic acids, arylphosphonic acids, aliphatic carboxylic acids and aromatic carboxylic acids.

Generally, after color development, the photographic emulsion layer is bleached. The bleaching may be carried out simultaneously with fixing as a monobath bleach-fixing treatment, or the bleaching and the fixing steps can be carried out separately. Further, in order to conduct a rapid overall processing, bleach-fixing can be performed either after the bleaching or after the fixing. Generally, the bleaching solution or the bleach-fixing solution in the present invention uses, as a bleaching agent, an aminopolycarboxylic acid iron complex salt. The bleaching solution or the bleach-fixing solution used in the present invention can contain various additive compounds as described in Japanese Patent Application (OPI) No. 215272/87, pages 22 to 30. After the desilvering step (bleach-fixing or bleaching), washing and/or stabilizing is carried out. It is preferred to use, for washing water or for a stabilizing solution, water which has been subjected to water softening treatment, such as a method using an ion exchange resin or a reverse osmosis apparatus as described in Japanese Patent Application No. 131632/86. More specifically, the method as described in Japanese Patent Application (OPI) No. 131632/86 is preferably used.

Further, suitable additives which can be used in a washing step and a stabilizing step include various compounds as described in Japanese Patent Application (OPI) No. 215272/87, pages 30 to 36.

It is preferable that the amount of the replenishing solution in each step is small. Preferably the amount of the replenishing solution is from about 0.1 to about 50 times, more preferably from 3 to 30 times the amount of the solution carried over from the preceding bath per unit area of the light-sensitive material.

In the case of using DRR compounds, any silver halide developing agent (or electron donor) which is capable of cross-oxidation of the DRR compounds may be employed in the present invention. These silver halide developing agents may be incorporated into an alkaline developing solution (processing element) having a pH of 12 to 14 or in an appropriate layer of the photographic element. Examples of developing agents suitable for use in the present invention are illustrated below: hydroquinone, aminophenols (e.g., N-methylaminophenol), 1-phenyl-3-pyrazolidone, 1-phenyl-4,4-dimethyl-3-pyrazolidone, 1-phenyl-4-methyl-4-hydroxymethyl-3-pyrazolidone, N,N-diethyl-p-phenylenediamine, 3-methyl-N,N-diethyl-p-phenylenediamine, 3-methoxy-N-ethoxy-p-phenylenediamine, etc.

Of these, black-and-white developing agents capable of reducing stains of an image-receiving layer (mordant layer) are generally particularly preferably the same as described above with respect to the aforesaid alkaline development processing solution.

In applying the light-sensitive material in accordance with the present invention to diffusion transfer process type film units, a viscous developing solution is preferably used. Such a viscous developing solution is a liquid composition containing processing components necessary for developing silver halide emulsions (and forming a diffusion-transferred dye image), in which water is a main solvent, with a hydrophilic solvent such as methanol or methylcellosolve being sometimes present. This processing composition preferably contains a hydrophilic polymer such as high molecular weight polyvinyl alcohol, hydroxyethyl, cellulose, sodium carboxymethylcellulose, etc. These polymers are used so as to impart a viscosity of about 1 poise or more, preferably from about 500 to 1,000 poises, to the processing composition.

The above-described processing composition preferably fills a pressure-rupturable container to be used as described in U.S. Pat. Nos. 2,543,181, 2,643,886, 2,653,732, 2,723,051, 3,056,491, 3,056,492, and 3,152,515, etc.

In accordance with the present invention, direct positive images having high Dmax and low Dmin are obtained with the use of the specific nucleating agent represented by formula (I), even when processed with a developing solution having a comparatively low pH.

When the nucleating agent represented by formula (I) according to the present invention is used, adverse effects on spectral sensitization do not occur, and direct positive images having good graininess are obtained even when processed with an exhausted running solution.

Further, when the photographic light-sensitive material containing the nucleating agent represented by formula (I) according to the present invention is subjected to development processing after having been preserved under high temperature and/or high humidity conditions, decrease in Dmax and increase in Dmin are hardly observed as compared with the case in which the photographic light-sensitive material is processed just after its production.

| Developing Solution X: | |
|---|---|
| Sodium sulfite | 30 g |
| Hydroquinone | 10 g |
| 1-Phenyl-4-methyl-4-hydroxymethyl-3-pyrazolidone | 0.75 g |
| Trisodium phosphate | 40 g |
| Sodium hydroxide | 10.7 g |
| 5-Methylbenzotriazole | 0.02 g |
| Water to make | 1 liter |

It is seen from the results shown in Table 1 that the nucleating agents according to the present invention show better reversal properties than the comparative compound.

TABLE 1

| Nucleating Agent | Amount Added (mmol/mol AgBr) | Dmax | Dmin | Note |
|---|---|---|---|---|
| None | — | 0.07 | 0.07 | Comparison |
| Compound (2) | 0.005 | 1.60 | 0.07 | Invention |
| Compound (23) | 0.004 | 1.95 | 0.08 | Invention |
| Compound (24) | 0.004 | 1.90 | 0.09 | Invention |
| Comparative Compound (A) | 0.004 | 1.50 | 0.12 | Comparison |

Comparative Compound (A): (disclosed in U.S. Pat. No. 4,471,044)

Moreover, advantageously high sensitivity is obtained upon adding the nucleating agent represented by formula (I) according to the present invention to a surface latent image type negative photographic light-sensitive material.

The present invention is now illustrated in greater detail by reference to the following Examples, but the present invention is not to be construed as being limited thereto. Unless otherwise indicated, all parts, percents, ratios and the like are by weight.

EXAMPLE 1

In manner analogous to that described in Japanese Patent Application (OPI) No. 95533/85, an internal latent image type direct positive silver bromide emulsion containing silver bromide grains which were internally chemically sensitized with sulfur and gold, and the surface of which was chemically sensitized with sulfur, was prepared. The grains were 1.0 μm octahedral grains. To this emulsion was added the nucleating agent represented by formula (I) of the present invention or a nucleating agent as disclosed in U.S. Pat. No. 4,471,044 (for comparison), and each of the resulting solutions was coated on a cellulose acetate film support in a silver amount of 4.4 g/m² and a gelatin amount of 4.9 g/m² together with a protective layer (gelatin: 0.8 g/m²). Each of the thus coated samples was exposed to 1,000 lux tungsten light for 1/10 second through a wedge of continuous gradation, then processed with Developing Solution X (surface developer: pH=13.5) having the following composition. Maximum density (Dmax) and minimum density (Dmin) of the thus obtained direct reversal images are shown in Table 1 below.

EXAMPLE 2

To the same internal latent image type direct positive emulsion as described in Example 1 was added the nucleating agent represented by formula (I) of the present invention or Comparative Compound (A), and coated samples were prepared in the same manner as described in Example 1 using the resulting emulsions. These samples were imagewise exposed under the same exposure conditions as described in Example 1, and processed with Developing Solution Y of the following composition having a lower pH (pH=10.7) than Developing Solution X. Maximum density (Dmax) and minimum density (Dmin) of the thus obtained direct reversal images are shown in Table 2 below.

| Developing Solution Y: | |
|---|---|
| Sodium sulfite | 30 g |
| hydroquinone | 10 g |
| 1-Phenyl-4-methyl-4-hydroxymethyl-3-pyrazolidone | 0.75 g |
| Trisodium phosphate | 40 g |
| 5-Methylbenzotriazole | 0.02 g |
| Water to make | 1 liter |

It is seen from the results shown in Table 2 that the compounds according to the present invention show better reversal properties than Comparative Compound (A) at a lower pH level as well.

TABLE 2

| Nucleating Agent | Amount Added (mmol/mol AgBr) | Dmax | Dmin | Note |
|---|---|---|---|---|
| None | — | 0.04 | 0.04 | Comparison |
| Compound (2) | 0.120 | 2.05 | 0.06 | Invention |
| Compound (23) | 0.095 | 2.15 | 0.07 | Invention |
| Compound (24) | 0.095 | 2.03 | 0.08 | Invention |
| Comparative Compound (A) | 0.095 | 1.80 | 0.08 | Comparison |

EXAMPLE 3

On a polyethylene terephthalate transparent support were coated in order the following layers to prepare four kinds of Color Direct Positive Light-Sensitive Material Sheets (A) to (D).

(1) Mordanting layer containing the following copolymer (3.0 g/m$^2$) and gelatin (3.0 g/m$^2$).

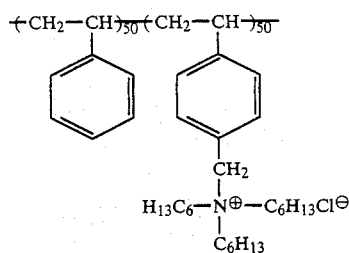

(2) White reflecting layer containing titanium oxide (18 g/m$^2$) and gelatin (2.0 g/m$^2$).

(3) Light shielding layer containing carbon black (2.0 g/m$^2$) and gelatin (1.0 g/m$^2$).

(4) Layer containing the magenta DRR compound of the following structural formula I (0.21 g/m$^2$), the magenta DRR compound of the structural formula II (0.11 g/m$^2$), tricyclohexyl phosphate (0.08 g/m$^2$), 2,5-di-tert-pentadecylhydroquinone (0.009 g/m$^2$), and gelatin (0.9 g/m$^2$).

Structural Formula I:

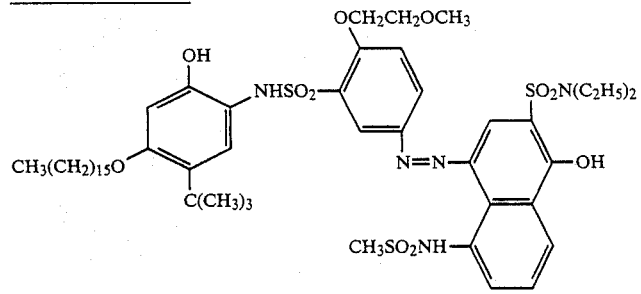

Structural Formula II:

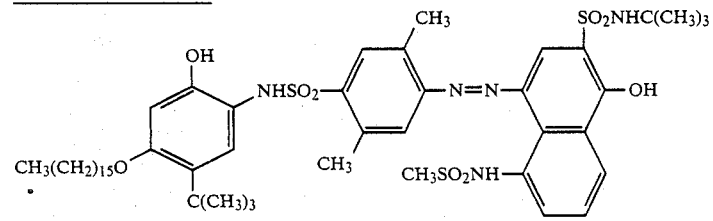

(5) Green-sensitive emulsion layer containing a dye-sensitized internal latent image type direct positive silver bromide emulsion (0.82 g/m$^2$ in terms of silver amount), gelatin (0.9 g/m$^2$), 2-sulfo-5-n-pentadecylhydroquinone sodium salt (0.08 g/m$^2$), and the nucleating agent of the present invention (as shown in Table 3) for each light-sensitive material sheet ($10^{-10}$ mol to $10^{-9}$ mol per g of emulsion).

(6) Protective layer containing gelatin (1.0 g/m$^2$).

The above-described Light-Sensitive Material Sheets (A) to (D) were combined with a processing element and a cover sheet as described below, and were then subjected to exposure and development processing.

Processing Element

| Processing Solution: | | |
|---|---|---|
| 1-Phenyl-4-methyl-4-hydroxymethyl-3-pyrazolidone | 8.0 | g |
| tert-Butylhydroquinone | 0.1 | g |
| 5-Methylbenzotriazole | 2.5 | g |
| Benzyl alcohol | 1.5 | ml |
| Sodium sulfite (anhydrous) | 1.5 | g |
| Na salt of carboxymethyl cellulose | 61 | g |
| Zinc nitrate hexahydrate | 0.4 | g |
| Carbon black | 410 | g |
| Potassium hydroxide | 56 | g |
| H$_2$O | 260 | ml |

0.8 g portions of the processing solution having the above-described composition were retained in a "pressure-rupturable container".

Cover Sheet

A cover sheet was prepared by coating in order an acidic polymer layer (neutralizing layer) of polyacrylic acid (viscosity as 10 wt % aqueous solution: about 1,000 cp) (15 g/m$^2$) and a neutralization timing layer of acetyl cellulose (3.8 g/m$^2$) and styrene/maleic anhydride copolymer (molar ratio: styrene:maleic anhydride=about 60:40; molecular weight: about 50,000) (0.2 g/m$^2$) on a polyethylene terephthalate support.

Processing Steps

The above-described cover sheet was superposed on each of the aforesaid light-sensitive sheets (A) to (D), and wedge exposure was conducted for 1/100 second from the cover sheet side using a tungsten light source. Then, the above-described processing solution was spread in a thickness of 100 μm between the two sheets using pressure-applying rollers. The spread processing was conducted at 25° C. After the processing, green density of image formed in the image-receiving layer was measured 1 hour after the processing through the transparent support of the light-sensitive sheet using a Macbeth reflection densitometer. The results thus obtained are shown in Table 3 below.

It is seen from the results shown in Table 3 that the nucleating agents represented by formula (I) of the present invention show excellent reversal properties in instant color direct positive light-sensitive materials as well.

TABLE 3

| Light-Sensitive Material | Nucleating Agent | Amount Added (mmol/g emulsion) | Dmax | Dmin | note |
|---|---|---|---|---|---|
| A | None | — | 0.05 | 0.05 | Comparison |
| B | Compound (1) | $8.0 \times 10^{-6}$ | 1.95 | 0.07 | Invention |
| C | Compound (23) | $5.0 \times 10^{-6}$ | 2.15 | 0.08 | Invention |
| D | Compound (26) | $5.0 \times 10^{-6}$ | 2.17 | 0.07 | Invention |

| Composition of Developing Solution: | |
|---|---|
| Water | 500 ml |
| Metol | 2 g |
| Anhydrous sodium sulfite | 90 g |
| Hydroquinone | 8 g |
| Sodium carbonate monohydrate | 52.5 g |
| Potassium bromide | 5 g |
| Water to make | 1 liter |

A comparison of the sensitivity values shown in Table 4 clearly shows that the compounds according to the present invention have the effect of enhancing photographic sensitivity when compared to Comparative Compound (A).

TABLE 4

| Nucleating Agent | Amount Added (mmol/kg emulsion) | Relative Sensitivity | Fog Density | Note |
|---|---|---|---|---|
| none | — | 100 (standard) | 0.04 | Comparison |
| Compound (4) | $4.0 \times 10^{-3}$ | 145 | 0.04 | Invention |
| Compound (27) | $4.0 \times 10^{-3}$ | 163 | 0.04 | Invention |
| Comparative Compound (A) | $4.0 \times 10^{-3}$ | 141 | 0.04 | Comparison |

Sensitizing Dye E:

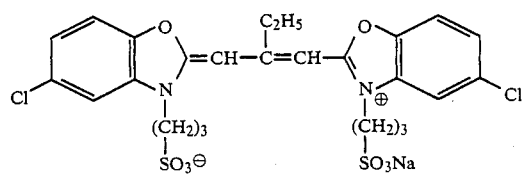

EXAMPLE 4

An emulsion prepared by adding Sensitizing Dye E ($9.5 \times 10^{-5}$ mol) and the nucleating agent of the present invention (as shown in Table 4) or Comparative Compound (A) to 1 kg of a silver bromide emulsion prepared in a conventional manner (having a (100) plane) was coated on a triacetate film support, and dried to obtain photographic light-sensitive materials.

The photographic light-sensitive materials were exposed through an optical wedge (for 0.1 second) at 3,200 lux using a light source fitted with a yellow filter (SC-46, manufactured by Fuji Photo Film Co., Ltd.).

The thus-exposed materials were developed at 20° C. for 5 minutes using a developing solution of the following composition, and were subjected to conventional stopping, fixing, and washing steps to obtain strips with a given black-and-white image. Density of the image was measured using a densitometer, model TCD, manufactured by Fuji Photo Film Co., Ltd., to obtain yellow filter sensitivity ($S_y$) and fog value. The results thus obtained are shown in Table 4 below as relative values taking the point of (fog+0.10) as a standard point of optical density for determining sensitivity.

Internal latent image type emulsions A and B used in the examples below were prepared in the following manner.

Emulsion A

An aqueous solution of potassium bromide and an aqueous solution of silver nitrate were simultaneously added at 75° C. over a period of about 20 minutes with vigorous stirring to an aqueous gelatin solution containing 0.3 g of 3,4-dimethyl-1,3-thiazoline-2-thion per mol of Ag to obtain an octahedral monodispersed silver bromide emulsion having an average grain diameter of 0.4 μm. 6 mg each of sodium thiosulfate and chloroauric acid (tetrahydrate) were added to the emulsion per mol of silver and the emulsion was heated at 75° C. for 80 minutes to be chemically sensitized. The thus prepared silver bromide grains were used as cores and were treated for a further 40 minutes under the same precipitation conditions as above described to further grow, shells thereby finally producing an octahedral monodispersed core/shell silver bromide emulsion having an average grain diameter of 0.7 μm. To the emulsion were added 1.5 mg of each of sodium thiosulfate and chloroauric acid (tetrahydrate) per mol of silver, and the emulsion was heated at 60° C. for 60 minutes to be chemically sensitized thereby producing an internal latent image type silver halide emulsion A.

Emulsion B

An aqueous solution containing potassium bromide and sodium chloride and an aqueous solution of silver nitrate were simultaneously added with vigorous stirring to an aqueous gelatin solution containing 0.5 g of 3,4-dimethyl-1,3-thiazoline-2-thione per mol of Ag, at 55° C. over a period of about 5 minutes to produce a monodispersed silver chlorobromide emulsion (silver bromide content: 40 mol %) having an average grain diameter of about 0.2 μm. To the emulsion were added 35 mg of sodium thiosulfate and 20 mg of chloroauric acid (tetrahydrate), and the emulsion was chemically sensitized by heating at 55° C. for 60 minutes. Using the thus obtained silver chlorobromide grains as cores, the silver chlorobromide grains were further treated for 40 minutes under the same precipitation conditions as above to grow shells, thereby finally obtaining a monodispersed core/shell silver chlorobromide emulsion (silver bromide content: 40 mol %) having an average grain diameter of 0.4 μm. A coefficient of variation on grain size was about 15%. To the emulsion were added 3 mg of sodium thiosulfate and 3.5 mg of chloroauric acid (tetrahydrate) per mol of silver, and the emulsion was chemically sensitized by heating at 60° C. for 50 minutes to produce an internal latent image type silver halide emulsion B.

EXAMPLE 5

On a paper support, both surface of which were laminated with polyethylene, were coated layers having the compositions shown below to prepare a multilayer color photographic light-sensitive material having the layer structure as follows.

Layer Structure:

| | |
|---|---|
| E9 Layer | Protective Layer |
| E8 Layer | Ultraviolet ray absorbing layer |
| E7 Layer | Blue-sensitive emulsion Layer |
| E6 Layer | Ultraviolet ray absorbing layer |
| E5 Layer | Yellow filter layer |
| E4 Layer | Ultraviolet ray absorbing layer |
| E3 Layer | Green-sensitive emulsion layer |
| E2 Layer | Ultraviolet ray absorbing layer |
| E1 Layer | Red-sensitive emulsion layer |
| Support | |
| B1 Layer | Anti-curling layer |
| B2 Layer | Protective layer |

Coating solutions were prepared in the following manner.

Preparation of a coating solution for E1 Layer:

13.4 g of a cyan coupler (Ex CC-1), 5.7 g of a color image stabilizer (Ex SA-1) and 10.7 g of a polymer (Ex P-1) were dissolved in 40 ml of ethyl acetate and 7.7 ml of a solvent (Ex S-1), and the solution was emulsified and dispersed in 185 ml of a 10% aqueous gelatin solution containing 8 ml of a 10% aqueous solution of sodium dodecylbenzenesulfonate to prepare an emulsified dispersion. Separately, to the internal latent image type silver halide emulsion B (containing 63 g of Ag/kg) was added a red-sensitizing dye shown below in an amount of $2.5 \times 10^{-4}$ mol per mol of silver. The emulsified dispersion described above and the silver halide emulsion were mixed and dissolved to prepare a coating solution for E1 Layer having the composition shown below.

Coating solutions for E2 Layer to E9 Layer and B1 Layer and B2 Layer were prepared in the same manner as the coating solution for E1 Layer, but having the specific ingredients shown below. As a gelatin hardener, 2-oxy-3,5-dichloro-s-triazine sodium salt was used in each layer.

Spectral sensitizing dyes used for each emulsion layer were as follows:

Red-sensitive emulsion layer:

A mixture (2:1 by molar ratio) of

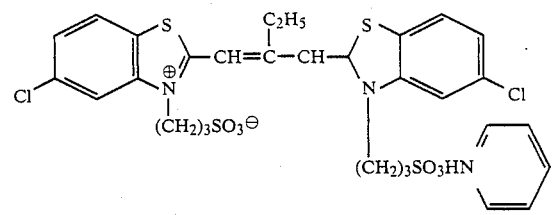

and

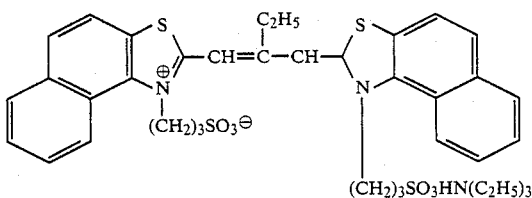

($2.5 \times 10^{-4}$ mol per mol of silver halide)

Green-sensitive emulsion layer:

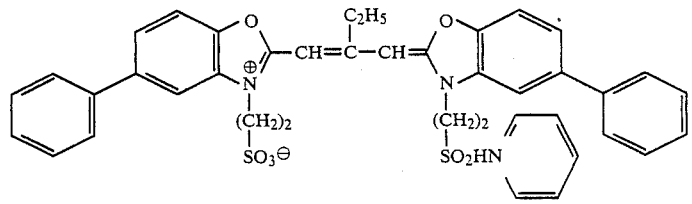

($3.1 \times 10^{-4}$ mol per mol of silver halide)

Blue-sensitive emulsion layer:

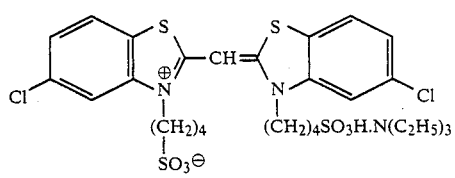

($4.3 \times 10^{-4}$ mol per mol of silver halide)

The following dyes were used as irradiation preventing dyes.

Irradiation preventing dye for the green-sensitive emulsion layer:

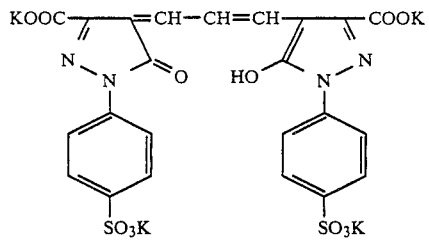

Irradiation preventing dye for the red-sensitive emulsion layer:

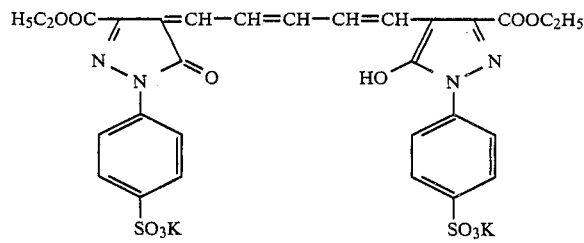

Compositions of Layers:

The composition of each layer is shown below. The coated amount of each component is illustrated in weight per m². The coated amounts of silver halide emulsion and colloidal silver are shown in the term of silver.

Support:

Polyethylene-laminated paper (containing a white pigment (e.g., $TiO_2$) and a bluing dye (e.g., ultramarine) in the polyethylene layer on E1 Layer side).

| E1 Layer: | |
|---|---|
| Silver halide emulsion B | 0.39 g |
| Gelatin | 1.35 g |
| Cyan coupler (Ex CC-1) | 0.40 g |
| Color image stabilizer (Ex SA-1) | 0.17 g |
| Polymer (Ex P-1) | 0.32 g |
| Solvent (Ex S-1) | 023 g |
| Development controlling agent (Ex GC-1) | 32 mg |
| Stabilizer (Ex A-1) | 5.8 mg |
| Nucleation accelerating agent (EX ZS-1) | 0.37 mg |
| Nucleating agent shown in Table 5 below | |
| E2 Layer: | |
| Gelatin | 1.6 g |
| Ultraviolet ray absorbing agent (Ex UV-1) | 0.62 g |
| Color mixing preventing agent (Ex KB-1) | 0.06 g |
| Solvent (Ex S-2) | 0.24 g |
| E3 Layer: | |
| Silver halide emulsion B | 0.27 g |
| Gelatin | 1.79 g |
| Magenta coupler (Ex MC-1) | 0.32 g |
| Color image stabilizer (Ex SA-2) | 0.20 g |
| Solvent (Ex S-3) | 0.65 g |
| Development controlling agent (EX GC-1) | 22 mg |
| Stabilizer (Ex A-1) | 4 mg |
| Nucleation accelerting agent (Ex ZS-1) | 0.26 mg |
| Nucleating agent shown in Table 5 below | |
| E4 Layer: | |
| Gelatin | 0.53 g |
| Ultraviolet ray absorbing agent (Ex UV-1) | 0.21 g |
| Color mixing preventing agent (Ex KB-2) | 0.02 g |
| Solvent (Ex S-2) | 0.08 g |
| E5 Layer: | |
| Colloidal silver | 0.10 g |
| Gelatin | 0.53 g |
| Ultraviolet ray absorbing agent (Ex IV-1) | 0.21 g |
| Color mixing preventing agent (Ex KB-2) | 0.02 g |
| Solvent (Ex S-2) | 0.08 g |
| E6 Layer: | |
| Same as E4 Layer | |
| E7 Layer: | |
| Silver halide emulsion B | 0.26 g |
| Gelatin | 1.83 g |
| Yellow coupler (Ex YC-1) | 0.83 g |
| Color image stabilizer (Ex SA-3) | 0.19 g |
| Solvent (Ex S-4) | 0.35 g |
| Development controlling agent (Ex GC-1) | 32 mg |
| Stabilizer (Ex A-1) | 2.9 mg |
| Nucleation accelerating agent (Ex ZS-1) | 0.2 mg |
| Nucleating agent shown in Table 5 below | |
| E8 Layer: | |
| Gelatin | 0.53 g |
| Ultraviolet ray absorbing agent (Ex IV-1) | 0.21 g |
| Solvent (Ex S-3) | 0.08 g |
| E9 Layer: | |
| Gelatin | 1.33 g |
| Acryl-modified copolymer of polyvinyl alcohol (degree of modification: 17%) | 0.17 g |
| Liquid paraffin | 0.03 g |
| Latex particles of polymethyl methacrylate (average particle diameter: 2.8 μm) | 0.05 g |
| B1 Layer: | |
| Gelatin: | 8.7 g |
| B2 Layer: | |
| Same as E9 Layer | |

The chemical structures and names of the compounds used are shown below.

-continued
Cyan coupler (Ex CC-1):
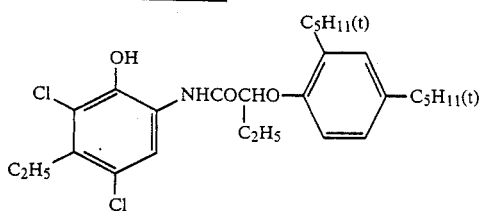
Magenta coupler (Ex MC-1):
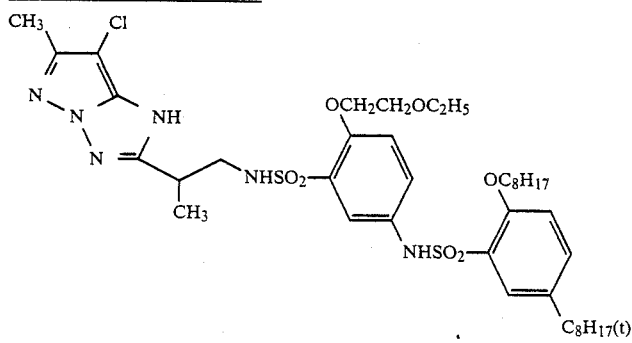
Yellow coupler (Ex YC-1):
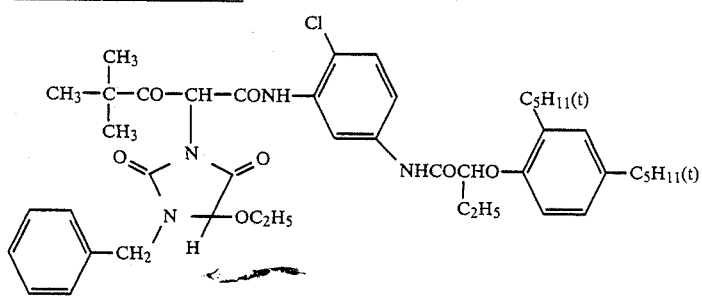
Color image stabilizer (Ex SA-1):
A mixture (5:8:9 by weight ratio) of
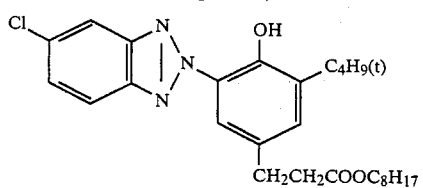
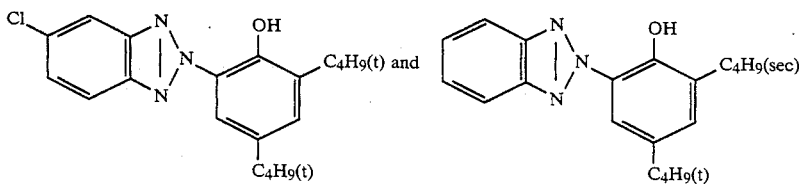
Color image stabilizer (Ex SA-2):
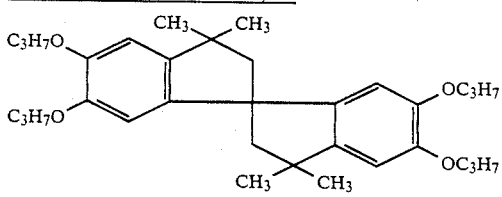

Color image stabilizer (Ex SA-3):
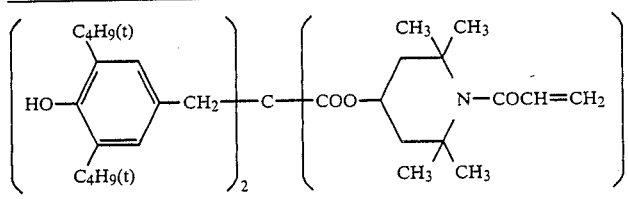
Polymer (Ex P-1):
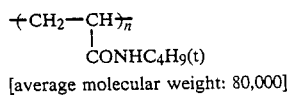
[average molecular weight: 80,000]
Solvent (Ex S-1):
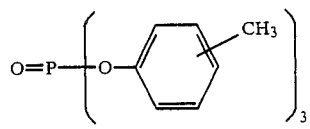
Solvent (Ex S-2):
$O=P(O-C_9H_{11}(iso))_3$
Solvent (Ex S-3):
A mixture (2:1 by volume ratio) of
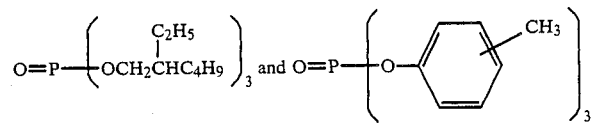
Solvent (Ex S-4):
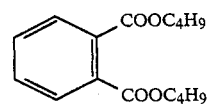
Ultraviolet ray absorbing agent (Ex UV-1):
A mixture (2:9:8 by weight ratio) of
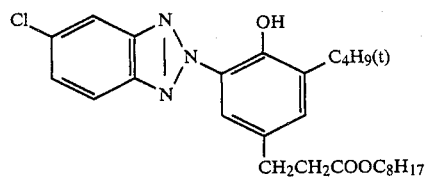
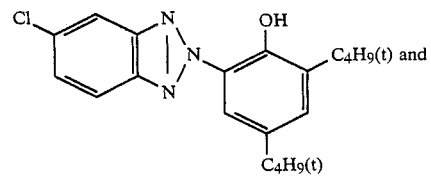
Color mixing preventing (Ex KB-1):
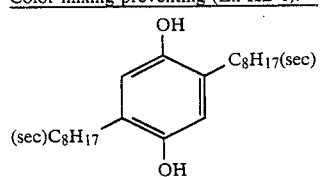

Color mixing preventing (Ex KB-2):

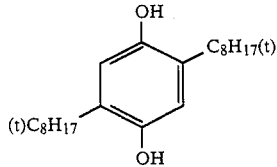

Development controlling agent (Ex GC-1):

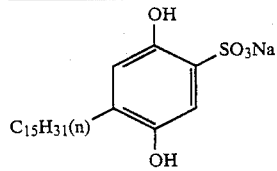

Stabilizer (Ex A-1):

4-Hydroxy-6-methyl-1,3,3a,7-tetraazaindene

Nucleation accelerating agent (Ex ZS-1):

2-(3-Dimethylaminopropylthio)-5-mercapto-1,3,4-thiadiazole hydrochloride

The color printing papers thus prepared were preserved under conditions of 40° C. and 80% RH (relative humidity) for 2 days (incubation), then wedge-exposed (for 1/10 second, in 10 CMS, at color temperature of 3200° K.) and subjected to Processing Step A shown below to obtain magenta color images. The densities of the color images were measured. The results thus obtained are shown in Table 5 below.

| Processing Step A: | Time | Temperature |
|---|---|---|
| Color Development | 1 min. 40 sec. | 37° C. |
| Bleach-Fixing | 40 sec. | 37° C. |
| Stabilizing (1) | 30 sec. | 37° C. |
| Stabilizing (2) | 30 sec. | 37° C. |

The replenishing method of the stabilizing bath was a so-called countercurrent replenishing system, i.e., the replenishing solution was supplied to stabilizing bath (2), the overflow from stabilizing bath (2) was introduced into stabilizing bath (1).

The composition of each processing solution used was as follows.

| Color developing solution: | Mother Solution |
|---|---|
| Diethylenetriaminepentaacetic acid | 2.0 g |
| Benzyl alcohol | 12.8 g |
| Diethylene glycol | 3.4 g |
| Sodium sulfite | 2.0 g |
| Sodium bromide | 0.26 g |
| Hydroxylamine sulfate | 2.60 g |
| Sodium chloride | 3.20 g |
| 3-Methyl-4-amino-N—ethyl-N—(β-methanesulfonamidoethyl)aniline | 4.25 g |

| Color developing solution: | Mother Solution |
|---|---|
| Potassium carbonate | 30.0 g |
| Fluorescent brightening agent (stilbene type) | 1.0 g |
| Water to make | 1000 ml |
| pH | 10.20 |

The pH was adjusted using potassium hydroxide or hydrochloric acid.

| Bleach-fix solution: | Mother Solution |
|---|---|
| Ammonium thiosulfate | 110 g |
| Sodium hydrogensulfite | 10 g |
| Ammonium iron (III) diethylenetriaminepentaacetate monohydrate | 56 g |
| Disodium ethylenediaminetetraacetate dihydrate | 5 g |
| 2-mercapto-1,3,4-triazole | 0.5 g |
| Water to make | 1000 ml |
| pH | 6.5 |

The pH was adjusted using aqueous ammonia or hydrochloric acid.

Washing water for stabilizing bath:

City (tap) water was passed through a mixed bed type column filled with an H type strong acidic cation exchange resin (Diaion SK-1B manufactured by Mitsubishi Chemical Industries Ltd.) and an OH type strong basic anion exchange resin (Diaion SA-10A manufactured by Mitsubishi Chemical Industries Ltd.) to prepare water having the water quality described below and then to which was added sodium dichloroisocyanulate in an amount of 20 mg per liter as a sterilizer.

| Calcium ion | 1.1 mg/l |
|---|---|
| Magnesium ion | 0.5 mg/l |
| pH | 6.9 |

TABLE 5

| No. | Nucleating Agent | Amount Added (mol/mol Ag) | Maximum Density | |
|---|---|---|---|---|
| | | | Before Incubation | After Incubation |
| 1 | Compound (1) | $2.5 \times 10^{-6}$ | 2.3 | 2.1 |
| 2 | " (2) | " | 2.1 | 2.0 |
| 3 | " (4) | " | 2.2 | 2.0 |
| 4 | " (8) | " | 2.1 | 2.0 |
| 5 | " (10) | " | 2.4 | 2.2 |
| 6 | " (11) | " | 2.2 | 2.1 |
| 7 | " (14) | " | 2.3 | 2.1 |
| 8 | " (16) | " | 2.1 | 2.0 |

TABLE 5-continued

| No. | Nucleating Agent | Amount Added (mol/mol Ag) | Maximum Density Before Incubation | Maximum Density After Incubation |
|---|---|---|---|---|
| 9 | " (23) | " | 2.4 | 2.3 |
| 10 | " (24) | " | 2.4 | 2.3 |
| 11 | " (26) | " | 2.2 | 2.1 |
| 12 | " (29) | " | 2.3 | 2.1 |
| 13 | " (30) | " | 2.3 | 2.1 |
| 14 | " (31) | " | 2.3 | 2.1 |
| 15 | " (32) | " | 2.3 | 2.2 |
| 16 | Compound (23) | $5.6 \times 10^{-7}$ | 2.3 | 2.1 |
| 17 | " " | $5.6 \times 10^{-6}$ | 2.4 | 2.3 |
| 18 | " " | $2.5 \times 10^{-5}$ | 2.4 | 2.3 |
| 19 | " " | $8.5 \times 10^{-5}$ | 2.4 | 2.3 |
| 20 | Comparative Compound (A) | $2.5 \times 10^{-6}$ | 1.7 | 1.2 |
| 21 | " (B) | " | 1.5 | 0.6 |
| 22 | " (B) | $2.5 \times 10^{-6}$ | 1.7 | 0.9 |
| 23 | None | — | 0.1 | 0.1 |

Comparative Compound (A) 6-Ethoxythiocarbonylamino-2-methyl-1-propargylquinolinium trifluoromethanesulfonate
Comparative Compound (B) 2-methyl-1-propargylquinolinium trifluoromethanesulfonate It can be seen from the results shown in Table 5 that Sample Nos. 1 to 19 containing the nucleating agent represented by formula (I) according to the present invention are preferred since they exhibit high maximum image density and small decrease in density by incubation in comparison with Samples 20 to 23 for comparison.

Further, the equivalent results were obtained when cyan and yellow image densities were measured.

EXAMPLE 6

Example 5 was repeated except using the internal latent image type emulsion A in place of the internal latent image type emulsion B, and results equivalent to those in Example 5 were obtained.

EXAMPLE 7

Examples 5 and 6 were repeated except using Compound (3), (5), (6), (7), (15), (22), (25) or (34) according to the present invention as a nucleating agent, respectively, and results equivalent to those in Examples 5 and 6 were obtained, respectively.

EXAMPLE 8

Example 5 was repeated except changing the nucleation accelerating agent to Nucleation Accelerating Agents (A-2), (A-5), (A-7), (A-8), (A-10), (A-12) or (A-14), and results equivalent to those in Example 5 were obtained.

EXAMPLE 9

Examples 5 and 6 were repeated except removing the nucleation accelerating agent and changing the color developing time to 2 minutes and 15 seconds, and results equivalent to those in Examples 5 and 6 were obtained, respectively.

EXAMPLE 10

Example 5 was repeated except changing the cyan coupler, magenta coupler and yellow coupler to a mixture (1:1 by molar ratio) of C-1 and C-5 each described below, M-12 illustrated hereinbefore and Y-9 illustrated hereinbefore, respectively, and results equivalent to those in Example 5 were obtained.

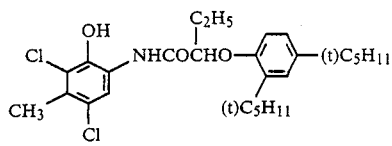

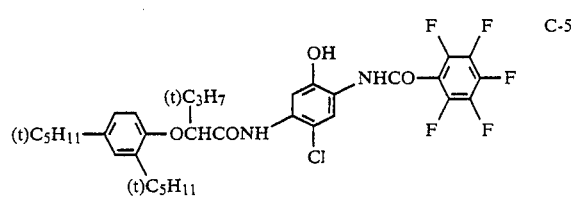

EXAMPLE 11

Examples 5 and 10 were repeated except that light of 0.5 lux (color temperature of 5400K) was used to expose the light-sensitive material surface for 10 seconds, beginning 15 seconds after the start of the color development and that the color developing time was changed to 1 minute and 25 seconds. Results equivalent to those in Examples 5 and 10 were obtained, respectively.

EXAMPLE 12

Examples 5 and 10 were repeated except changing the stabilizing bath to the stabilizing solution described below, and results equivalent to those in Examples 5 and 10 were obtained, respectively.

| Stabilizing solution: | Mother Solution |
|---|---|
| 1-Hydroxethylidene-1,1'-diphosphonic acid (60%) | 1.6 ml |
| Bismuth chloride | 0.35 g |
| Polyvinyl pyrrolidone | 0.25 g |
| Aqueous ammonia | 2.5 ml |
| Nitrilotriacetic acid · 3Na | 1.0 g |
| 5-Chloro-2-methyl-4-isothiazolin-3-one | 50 mg |
| 2-Octyl-4-isothiazolin-3-one | 50 mg |
| Fluorescent brightening agent (4,4'-diaminostilbene type) | 1.0 g |
| Water to make | 1000 ml |
| pH | 7.5 |

The pH was adjusted using potassium hydroxide or hydrochloric acid.

EXAMPLE 13

Example 5 was repeated except that the support was changed to a polyethylene terephthalate film and that the coated amounts of E1 Layer, E3 Layer and E7 Layer were increased to 1.4 times the coated amounts shown above. Results equivalent to those in Example 5 were obtained.

EXAMPLE 14

Examples 5 and 13 were repeated except for conducting the exposure to light and development processing using exposure and development apparatus as described in Japanese Patent Application (OPI) No. 231547/86, and results equivalent to those in Examples 5 and 13 were obtained, respectively.

EXAMPLE 15

On a paper support (thickness: 100 micron) having polyethylene laminated on both sides thereof were coated 1st to 14th layer on the surface of the support and 15th and 16th layer on the back side of the support to prepare a multilayer color photographic material. The polyethylene contains titanium dioxide as a white pigment and a slight amount of ultramarine as a blue dye on which the 1st layer is coated. (The surface chromaticities of the support were 88.0, -0.20, and -0.75 on L*, a*, and b* system.)

Composition of the light-sensitive layers:

The composition of each layer is shown below. The coated amount of each component was represented by g/m². The silver halide was represented by the amount of silver. The emulsion used in each layer was prepared in accordance with the preparation method of emulsion EM1 described below. However, a non-chemically ripened Lippmann emulsion was used as the emulsion for 14th layer.

| 1st Layer (Anti-halation layer) | |
|---|---|
| Black colloidal silver | 0.10 |
| Gelatin | 0.70 |
| 2nd Layer (Intermediate layer) | |
| Gelatin | 0.70 |
| 3rd Layer (Low sensitive red-sensitive layer) | |
| Silver bromide spectrally sensitized with the red sensitizing dye (ExS-1, 2, 3) (mean grain size 0.25μ, size distribution (variation coefficient) 8%, octahedron) | 0.04 |
| Silver chlorobromide spectrally sensitized with the red sensitizing dye (ExS-1, 2, 3) (silver chloride 5 mol %, mean grain size 0.40μ size distribution 10%, octahedron) | 0.08 |
| Gelatin | 1.00 |
| Cyan coupler (ExC-1, 2 in equivalent) | 0.30 |
| Descoloration inhibitor (Cpd-1, 2, 3, 4 in equivalent) | 0.18 |
| Stain inhibitor (Cpd-5) | 0.003 |
| Coupler dispersing medium (Cp-6) | 0.03 |
| Coupler solvent (Solv-1, 2, 3 in equivalent) | 0.12 |
| Nucleation accelerating agent (Cpd-22) | $2.0 \times 10^{-4}$ |
| Nucleating agent | shown in Table 6 below |
| 4th Layer (High sensitive red-sensitive layer) | |
| Silver bromide spectrally sensitized with the red sensitizing dye (ExS-1, 2, 3) (mean grain size 0.60μ, size distribution 15%, octahedron) | 0.14 |
| Gelatin | 1.00 |
| Cyan coupler (ExC-1, 2 in equivalent) | 0.30 |
| Discoloration inhibitor (Cpd-1, 2, 3, 4 in equivalent) | 0.18 |
| Coupler dispersing medium (Cpd-6) | 0.03 |
| Coupler solvent (Solv-1, 2, 3 in equivalent) | 0.12 |
| Nucleation accelerating agnet (Cpd-22) | $1.4 \times 10^{-4}$ |
| Nucleating agent | shown in Table 6 below |
| 5th Layer (Intermediate layer) | |
| Gelatin | 1.00 |
| Color mixing preventing agent (Cpd-7) | 0.08 |
| Solvent for Color mixing preventing agnet (Solv-4, 5 in equivalent) | 0.16 |
| Polymer latex (Cpd-8) | 0.10 |
| 6th Layer (Low sensitive green-sensitive layer) | |
| Silver bromide spectrally sensitized with the green sensitizing dye (ExS-4) (mean grain size 0.25μ, size distribution 8%, octahedron) | 0.04 |
| Silver chlorobromide spectrally sensitized with the green sensitizing dye (ExS-4) (silver chloride 5 mol %, mean grain size 0.40μ, size 10%, octahedron) | 0.06 |
| Gelatin | 0.80 |
| Magenta coupler (ExM-1, 2 in equivalent) | 0.11 |
| Discoloration inhibitor (Cpd-9) | 0.10 |
| Stain inhibitor (10:7:1 of Cpd-10, 11, 12, 13) | 0.025 |
| Coupler dispersing medium (Cpd-6) | 0.05 |
| Coupler solvent (Solv-4, 6 in equivalent) | 0.15 |
| Nucleation accelerating agnet (Cpd-22) | $1.3 \times 10^{-4}$ |
| Nucleating agent | shown in Table 6 below |
| 7th Layer (high sensitive green-sensitive layer) | |
| Silver bromide spectrally sensitized with the green sensitizing agent (ExS-4) (mean grain size 0.65μ, size distribution 16%, octadedron) | 0.10 |
| Gelatin | 0.80 |
| Magenta coupler (ExM-1, 2 in equivalent) | 0.11 |
| Discoloration inhibitor (Cpd-6) | 0.10 |
| Stain inhibitor (10:7:7:1 of Cpd-10, 11, 12, 13) | 0.025 |
| Coupler dispersing medium (Cpd-6) | 0.05 |
| Coupler solvent (Solv-4, 6 in equivalent) | 0.15 |
| Nucleation accelerating agnet (Cpd-22) | $1.5 \times 10^{-4}$ |
| Nucleating agent | shown in Table 6 below |
| 8th Layer (Intermediate layer) | |
| Same as 5th layer | |
| 9th Layer (Yellow filter layer) | |
| Yellow colloidal silver | 0.12 |
| Gelatin | 0.07 |
| Color mixing preventing agnet (Cpd-7) | 0.03 |
| Solvent for Color mixing preventing agent (Solv-4, 5 in equivaient) | 0.10 |
| Polymer latex (Cpd-8) | 0.07 |
| 10th Layer (Intermediate layer) | |
| Same as 5th layer | |
| 11th Layer (Low sensitive blue-sensitive layer) | |
| Silver bromide spectrally sensitized with the blue sensitizing dye (ExS-5, 6) (mean grain size 0.40μ, size distribution 8% octahedron) | 0.07 |

-continued

| | |
|---|---|
| Silver chlorobromide spectrally sensitized with the blue sensitizing dye (ExS-5, 6) (silver chloride 8 mol %, mean grain size 0.60μ, size distribution 11%, octahedron) | 0.14 |
| Gelatin | 0.80 |
| Yellow coupler (ExY-1) | 0.35 |
| Discoloration inhibitor (Cpd-14) | 0.10 |
| Stain inhibitor (1:5 of Cpd-5, 15) | 0.007 |
| Coupler dispersing medium (Cpd-6) | 0.05 |
| Couopler solvent (Solv-2) | 0.10 |
| Nucleation accelerating agnet (Cpd-22) | $1.8 \times 10^{-4}$ |
| Nucleating agent | shown in Table 6 below |
| 12th Layer (High sensitive blue-sensitive layer) | |
| Silver bromide spectrally sensitized with the blue sensitizing dye (ExS-5,6) (mean grain size 0.85, size distribution 18%, octahedron) | 0.15 |
| Gelatin | 0.60 |
| Yellow Coupler (ExY-1) | 0.30 |
| Discoloration inhibitor (Cpd-14) | 0.10 |
| Stain inhibitor (1:5 of Cpd-5, 15) | 0.007 |
| Coupler dispersing medium (Cpd-6) | 0.05 |
| Coupler solvent (Solv-2) | 0.10 |
| Nucleation accelerating agnet (Cpd-2) | $1.4 \times 10^{-4}$ |
| Nucleating agent | shown in Table 6 below |
| 13th Layer (Ultraviolet ray absorbing layer) | |
| Gelatin | 1.00 |
| Ultraviolet ray absorbing agnet (Cpd-2, 4, 16 in equivalent) | 0.50 |
| Color mixing preventing agnet (Cpd-7, 17 in equivalent) | 0.03 |
| Dispersing medium (Cpd 6) | 0.02 |
| Solvent for Ultraviolet ray absorbing agnet (Solv-2, 7 in equivalent) | 0.08 |
| Irradiation preventing dye (10:10:13:15 of Cpd-18, 19, 20, 21) | 0.04 |
| 14th Layer (Protective layer) | |
| Fine silver chlorobromide grain (Silver chloride 97 mol %, mean grain size 0.2μ) | 0.03 |
| Acryl-modified copolymer of polyvinyl alcohol | 0.01 |
| Polymethylmethacrylate particle (mean grain size 2.4μ) and Silicon oxide (mean grain size 5μ) in equivalent amount | 0.05 |
| Gelatin | 1.80 |
| Gelatin hardener (H-1, H-2 in equivalent) | 0.18 |
| 15th Layer (Backing layer) | |
| Gelatin | 2.50 |
| 16th Layer (Protective layer for backing layer) | |
| Polymethylmethacrylate particle (mean grain size 2.4μ) and Silicon oxide (mean grain size 5μ) in equivalent amount | 0.05 |
| Gelatin | 2.00 |
| Gelatin hardener (H-1, H-2 in equivalent) | 0.14 |

Preparation for Emulsion EM-1

An aqueous solution of potassium bromide and an aqueous solution of silver nitrate were simultaneously added at 75° C. over a period of 15 minutes with vigorous stirring to an aqueous gelatin solution to obtain an octahedral monodispersed silver bromide emulsion having an average grain diameter of 0.4 μm. 0.3 g of 3,4-dimethyl-1,3-thiazoline-2-thion, 6 mg of sodium thiosulfate and 7 mg of chloroauric acid (tetrahydrate) were subsequently added to the emulsion per mol of silver and the emulsion was heated at 75° C. for 80 minutes to be chemically sensitized. The thus prepared silver bromide grains were used as cores and were treated under the same precipitation conditions as above described to further grow shells, thereby finally producing an octahedral monodispersed core/shell silver bromide emulsion having an average grain diameter of 0.7 μm. The variation coeficient of the grain size was about 10%. To the emulsion were added 1.5 mg of each of sodium thiosulfate and chloroauric acid (hetrahydrate) per mol of silver, and the emulsion was heated at 60° C. for 60 minutes to be chemically sensitized, thereby producing an internal latent image type silver halide emulsion EM-1.

To each layer was added Alcanol XC (Du Pont de Nemerous) and sodium alkylbenzenesulfonate as an auxiliary emulsifying and dispersing agent, succinic acid ester and Magefac F-120 (made by Dainippon Ink & Chemicals, Inc.) as coating aid. To silver halide layers and cooildal silver layers were added Cpd-23, 24, 25 as a stabilizer. These samples were designated as Sample Nos. 15-01 to 15-19.

The chemical structures and names of the compounds used are shown below:

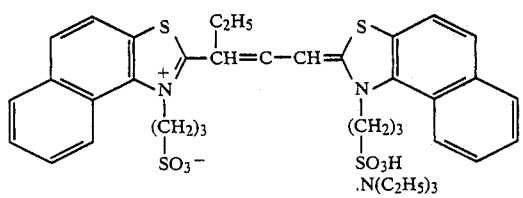

ExS-1

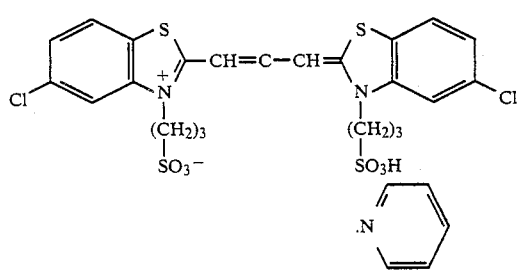

ExS-2

ExS-3
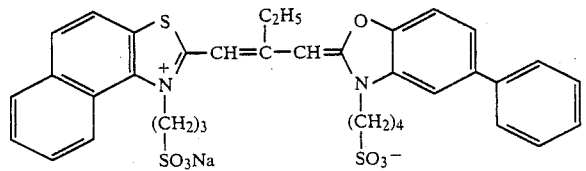
ExS-4
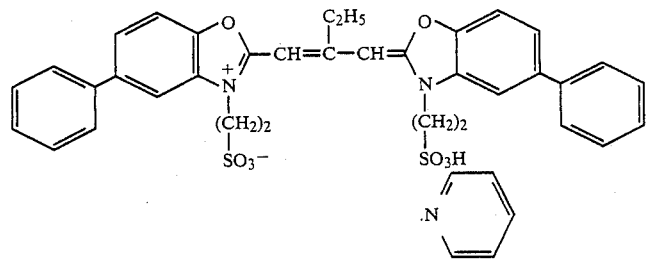
ExS-5
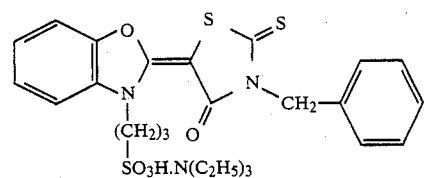
ExS-6
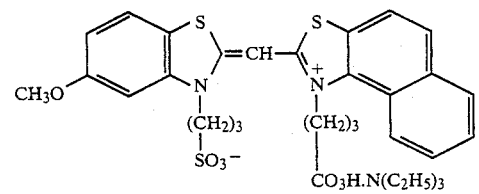
Cpd-1
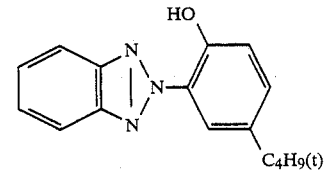
Cpd-2
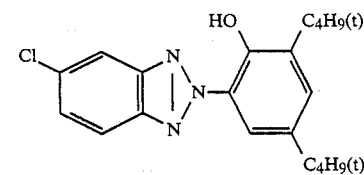
Cpd-3
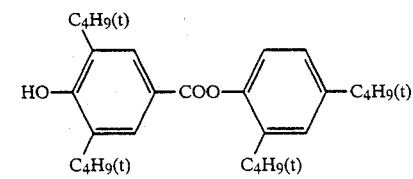
Cpd-4
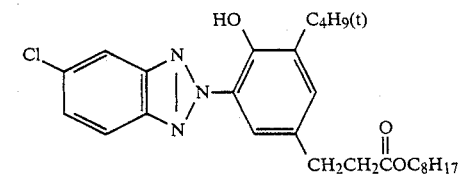

-continued
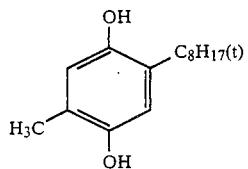 Cpd-5
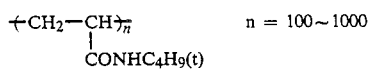 n = 100~1000  Cpd-6
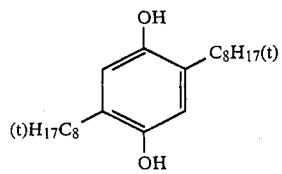 Cpd-7
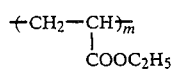 Cpd-8
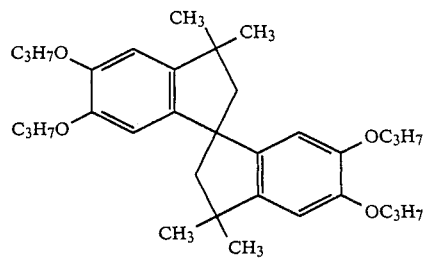 Cpd-9
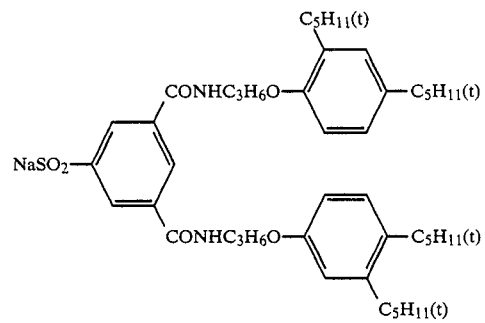 Cpd-10
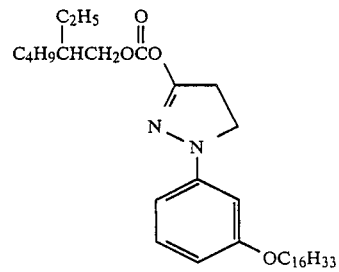 Cpd-11
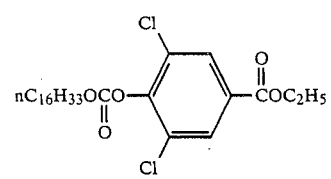 Cpd-12

-continued
Cpd-13
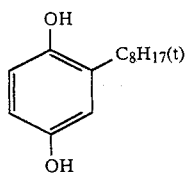
Cpd-14
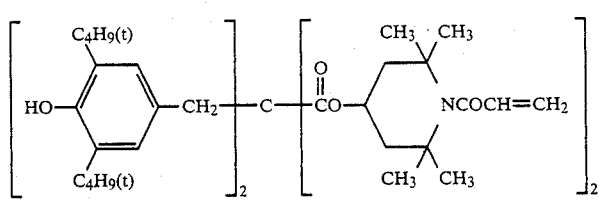
Cpd-15
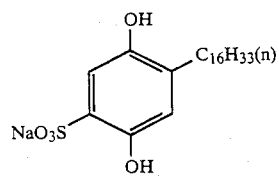
Cpd-16
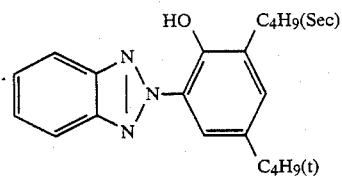
Cpd-17
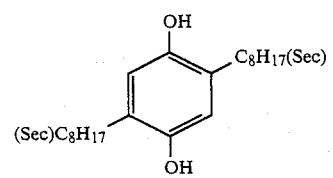
Cpd-18
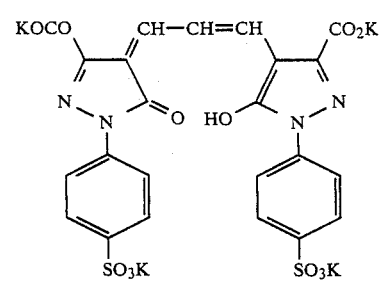
Cpd-19
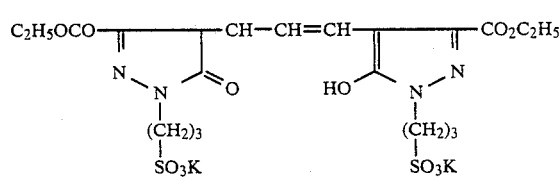
Cpd-20
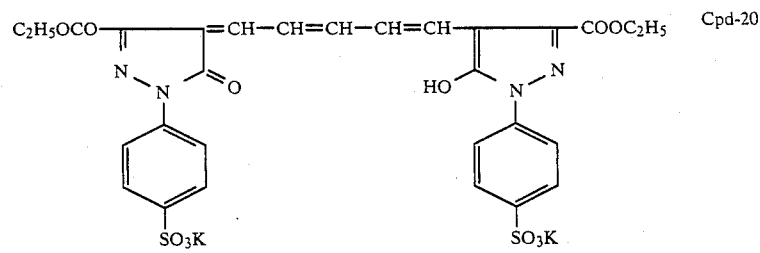

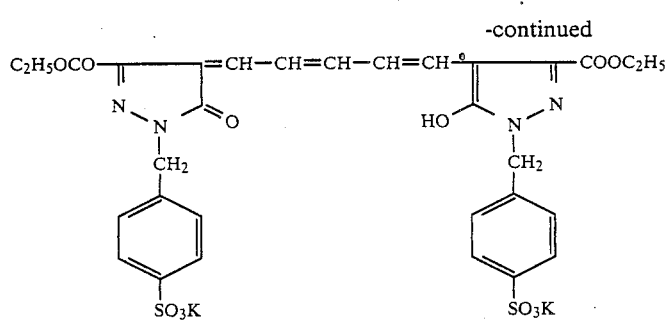
Cpd-21
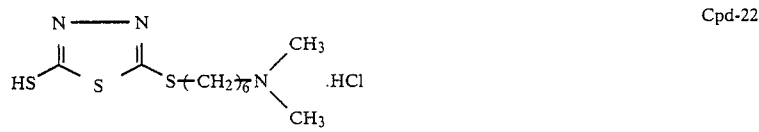
Cpd-22
Cpd-23
Cpd-24
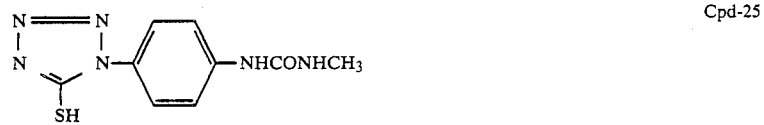
Cpd-25
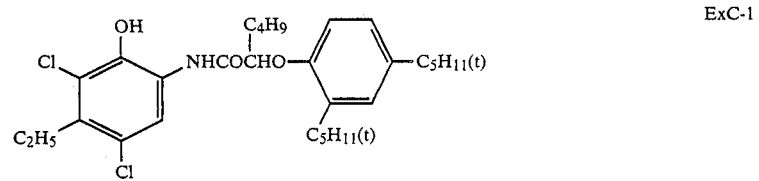
ExC-1
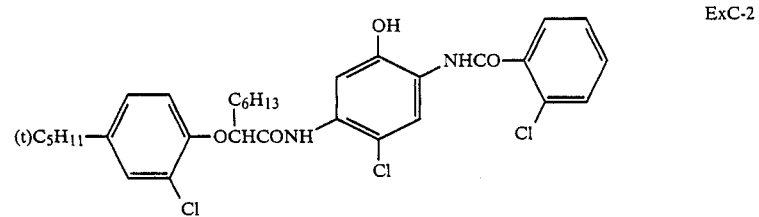
ExC-2
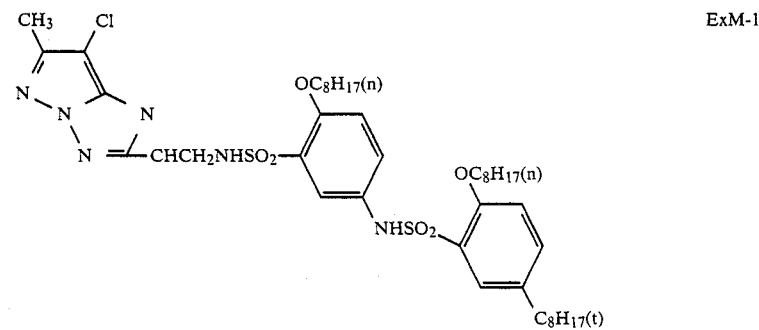
ExM-1

ExM-2

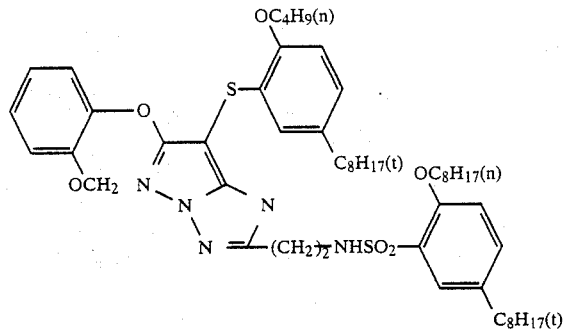

ExY-1

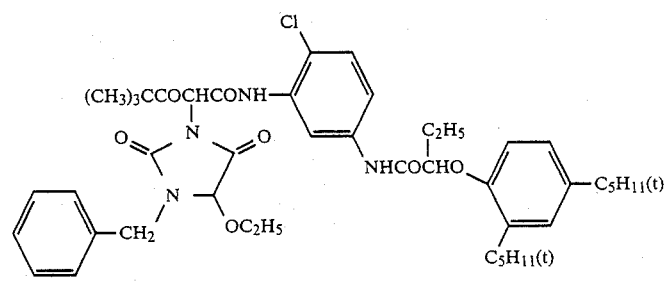

Solv-1: di(2-ethylhexyl)sebacate
Solv-2: trinonylphosphate
Solv-3: di(3-methylhexyl)phthalate
Solv-4: tricresylphosphate
Solv-5: dibutylphthalate
Solv-6: trioctylphosphate
Solv-7: di(2-ethylhexyl)phthalate
H-1: 1,2-bis(vinylsulfonylacetoamide)ethane
H-2: 4,6-dichloro-2-hydroxyl-1,3,5-triazine sodium salt The silver halide color photographic materials thus prepared were wedge-exposed (for 1/10 second, in 10 CMS, at color temperature of 3,200° K.) and subjected to Processing Step B as described below until the amount of the cumulative replenisher reaches the three times of the tank capacity. The results thus obtained are shown in Table 6 below to obtain magenta color images.

| Process-ing Step B | Time | Temperature (°C.) | Mother Solution Capacity (l) | Replenisher (ml/m²) |
|---|---|---|---|---|
| Color Development | 90 | 38 | 8 | 300 |
| Bleach-Fixing | 40 | 33 | 3 | 300 |
| Washing (1) | 40 | 33 | 3 | none |
| Washing (2) | 40 | 33 | 3 | none |
| Washing (3) | 15 | 33 | 0.5 | 320 |
| Drying | 30 | 80 | | |
| Drying | 30 | 80 | | |

The replenishing method of washing water was a so-called countercurrent replenishing system, i.e., the replenish solution was supplied to washing (3) bath, the overflow from washing (3) bath was introduced into washing (2) bath, the overflow from washing (2) bath was introduced into washing (1) bath. The carried over amount of the processed photographic material from bleach-fix bath to washing (1) bath was 35 ml/m². The magnifying power of the replenishing amount for washing to the carried over amount from bleach-fix bath was 9.1.

The composition of the each processing solution was as follows.

| Color developing solution: | Mother Solution | Replenisher |
|---|---|---|
| Ethylenediaminetetrakis methylenephosphonic acid | 0.5 g | 0.5 g |
| Diethylene glycol | 10 ml | 10 ml |
| Benzyl alcohol | 12.0 ml | 14.4 ml |
| Potassium bromide | 0.65 g | |
| Sodium sulfite | 2.4 g | 2.9 g |
| N,N—diethylhydroxylamine | 4.0 g | 4.8 g |
| Triethylenediamine-(1,4-diazabicyclo[2,2,2]octane) | 4.0 g | 4.8 g |
| N—ethyl-N—(β-methane-sulfoneamidoethyl)-3-methylaniline sulfate | 5.6 g | 6.6 g |
| Potassium carbonate | 27.0 g | 25.0 g |
| Fluorescent brightening agent (stilbene type) | 1.0 g | 1.2 g |
| Water to make | 1000 ml | 1000 ml |
| pH (25° C.) | 10.50 | 10.80 |

| Bleach-fix solution: | Mother Solution | Replenisher |
|---|---|---|
| Disodium ethylenediamine-tetraacetate dihydrate | 4.0 | Same as mother solution |
| Ammonium iron (III) ethylenediaminetetra-acetate dihydrate | 46.0 g | |
| Ammonium thiosulfate | 155 ml | |
| Sodium p-toluenesulfinate | 20.0 g | |
| Sodium sulfite | 12.0 g | |
| Ammonium bromide | 50.0 g | |
| Ammonium nitrate | 30.0 g | |
| Water to make | 1000 ml | |
| pH (25° C.) | 6.20 | |

Washing water (mother solution and replenisher):

City (tap) water was passed through a mixed bed type column filled with an H type strong acidic cation exchange resin (Amberlite IR-120B manufactured by Rohm & Haas Co.) and an OH type strong basic anion exchange resin (Amberlite IR-400 manufactured Rohm & Haas Co,) to prepare water having each concentration of calcium and magnesium of 3 mg/l or less, and to which was added sodium dichloroisocyanulate in an amount of 20 mg per litter and sodium sulfate in an amount of 1.5 g per liter. The pH of the washing water is within the range of 6.5 to 7.5.

TABLE 6

| No. | Nucleating Agent | Amount Added | Maximum Density | Minimum Density |
|---|---|---|---|---|
| 15-01 | Compound 1 | $2.0 \times 10^{-6}$ | 2.24 | 0.07 |
| 15-02 | 2 | " | 2.26 | 0.08 |
| 15-03 | 4 | " | 2.20 | 0.07 |
| 15-04 | 7 | " | 2.22 | 0.09 |
| 15-05 | 11 | " | 2.24 | 0.07 |
| 15-06 | 14 | " | 2.21 | 0.08 |
| 15-07 | 23 | " | 2.31 | 0.09 |
| 15-08 | 26 | " | 2.28 | 0.08 |
| 15-09 | 28 | " | 2.30 | 0.08 |
| 15-10 | 30 | " | 2.24 | 0.08 |
| 15-11 | 38 | " | 2.35 | 0.09 |
| 15-12 | 43 | " | 2.29 | 0.08 |
| 15-13 | 56 | " | 2.40 | 0.08 |
| 15-14 | 59 | " | 2.41 | 0.07 |
| 15-15 | 62 | " | 2.39 | 0.07 |
| 15-16 | 65 | " | 2.35 | 0.08 |
| 15-17 | Comparative compound (A) | " | 1.65 | 0.12 |
| 15-18 | Comparative compound (B) | " | 1.54 | 0.11 |
| 15-19 | none | — | 0.12 | 0.11 |

Comparative Compound (A):
6-Ethoxythiocarbonylamino-2-methyl-1-propargylquinolinium trifluoromethanesulfonate
Comparative Compound (B):
2-methyl-1-propargylquinolinium trifluoromethanesulfonate It can be seen from the results shown in Table 6 that Sample Nos. 15-01 to 15-16 containing the nucleating agent according to the present invention are preferred since they exhibit high maximum image density and low minimum image density in comparison with Sample Nos. 15-17 to 15-19 for comparison.

Further, the equivalent results were obtained when cyan and yellow image densities were measured.

EXAMPLE 16

Example 15 was repeated except using Processing Step C described below in place of Processing Step B, and equivalent results to those in Example 15 were obtained.

| Processing Step C | Time (sec) | Temperature (°C.) | Replenisher (ml/m²) |
|---|---|---|---|
| Color Development | 70 | 38 | 260 |
| Bleach-Fixing | 30 | 38 | 260 |
| Washing (1) | 30 | 38 | none |
| Washing (2) | 30 | 38 | 300 |

At this time, the magnifying power of the replenishing solution to washing water was 8.6.

| Color developing solution: | Mother Solution | Replenisher |
|---|---|---|
| Diethylenetriaminepentaacetic acid | 0.5 g | 0.5 g |
| 1-Hydroxyethylidene- | 0.5 g | 0.5 g |

| Color developing solution: | Mother Solution | Replenisher |
|---|---|---|
| 1,1-diphosphonic acid | | |
| Diethylene glycol | 8.0 g | 10.7 g |
| Benzyl alcohol | 9.0 g | 12.0 g |
| Sodium bromide | 0.7 g | none |
| Sodium chloride | 0.5 g | none |
| Sodium sulfite | 2.0 g | 2.4 g |
| Hydroxylamine sulfate | 2.8 g | 3.5 g |
| 3-methyl-4-amino-N—ethyl-N—(β-methanesulfonamidoethyl)aniline sulfate | 2.0 g | 2.5 g |
| 3-methyl-4-amino-N—ethyl-N—(β-hydroxyethyl)aniline sulfate | 4.0 g | 4.5 g |
| Potassium carbonate | 30.0 g | 30.0 g |
| Fluorescent brightening agent (stilbeve type) | 1.0 g | 1.2 g |
| Pure water to make | 1000 ml | 1000 ml |
| pH | 10.5 | 10.90 |

These pH were adjusted using potasssium hydroxide or hydrochloric acid.

| Bleach-fix solution: | Mother Solution | Replenisher |
|---|---|---|
| Ammonium thiosulfate | 77 g | 100 g |
| Sodium hydrogensulfite | 14.0 g | 21.0 g |
| Ammonium iron (III) ethylenediaminepentaacetate dihydrate | 40.0 g | 53.0 g |
| Disodium ethylenediaminetetraacetate dihydrate | 4.0 g | 5.0 g |
| 2-mercapto-1,3,4-triazole | 0.5 g | 0.5 g |
| pure water to make | 1000 ml | 1000 ml |
| pH | 7.0 | 6.5 |

These pH were adjusted using aqueous ammonia or hydrochloric acid.

Washing water (mother solution and replenisher):
Pure water was used.

While the invention has been described in detail and with reference to specific embodiments thereof, it will be apparent to one skilled in the art therein without departing from the spirit and scope thereof.

What is claimed is:

1. A silver halide photographic material comprising a support having thereon at least one light-sensitive silver halide photographic emulsion layer, wherein at least one layer selected from said at least one emulsion layer and other hydrophilic colloid layers contains at least one alkynyl substituted heterocyclic quaternary ammonium salt nucleating compound represented by the following general formula (I):

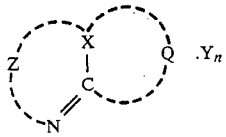

(I)

wherein Z represents a non-metallic atomic group necessary to form a substituted or unsubstituted 5-membered or 6-membered heterocyclic ring to which an aromatic ring or a heterocyclic ring may further be condensed; $R^1$ represents a substituted or unsubstituted aliphatic group; X represents

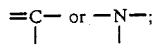

Q represents a non-metallic atomic group necessary to form a substituted or unsubstituted 4-membered to 12-membered non-aromatic hydrocarbon ring or a substituted or unsubstituted non-aromatic heterocyclic ring; at least one of $R^1$, a substituent for Z and a substituent for Q includes an alkynyl group; Y represents a counter ion necessary for charge balance; and n represents a number necessary to balance the charge.

2. A silver halide photographic material as in claim 1, wherein said material is a positive type photographic material, and wherein said at one least alkynyl substituted heterocyclic quaternary ammonium salt is present in at least one internal latent image-type silver halide photographic emulsion layer or at least one hydrophilic colloid layer adjacent thereto.

3. A silver halide photographic material as in claim 1, wherein said material is a negative type photographic material, and wherein said at least one alkynyl substituted heterocyclic quaternary ammonium salt is present in at least one surface latent image-type silver halide photographic emulsion layer or a hydrophilic colloid layer adjacent thereto.

4. A silver halide photographic material as in claim 1, wherein at least one of $R^1$, Z and Q includes a group capable of accelerating adsorption onto silver halide grains.

5. A silver halide photographic material as in claim 1, wherein the heterocyclic ring, including the optional condensed ring, which is completed with Z includes a quinolinium nucleus, a benzimidazolium nucleus, a pyridinium nucleus, an imidazolium nucleus, an indolenium nucleus, a pyrrolinium nucleus, a phenanthridium nucleus, an isoquinolinium nucleus and a naphthopyridinium nucleus, and said aliphatic group $R^1$ is an alkyl group, an alkenyl group or an alkynyl group.

6. A silver halide photographic material as in claim 1, wherein at least one of $R^1$, a substituent for Z or a substituent for Q contains an alkynyl group having from 2 to 18 carbon atoms which may be substituted.

7. A silver halide photographic material as in claim 4, wherein the adsorption acceleration group is connected as illustrated by the following general formula (II):

wherein in W represents a group capable of accelerating adsorption onto silver halide grains and is selected from among a thioamido group, a mercapto group and a 5-membered or 6-membered nitrogen-containing heterocyclic group; L represents a divalent linking group and m represents 0 or 1.

8. A silver halide photographic material as in claim 1, wherein said counter ion represented by Y is a monovalent or divalent anion or a cationic counter ion.

9. A silver halide photographic material as in claim 2, wherein said at least one alkynyl heterocyclic quaternary ammonium slat represented by formula (I) is present in an amount of from about $1 \times 10^{-8}$ mol to about 1 $10^{-2}$ mol per mol of silver in the silver halide emulsion.

10. A silver halide photographic material as in claim 9, wherein said amount is from $1 \times 10^{-7}$ mol to $1 \times 10^{-3}$ mol per mol of silver.

11. A silver halide photographic material as in claim 3, wherein said at least one alkynyl substituted heterocyclic quaternary ammonium salt represented by formula (I) is present in an amount of from about $1 \times 10^{-5}$ mol to about $1 \times 10^{-3}$ mol per mol of silver in the silver halide emulsion.

* * * * *

UNITED STATES PATENT AND TRADEMARK OFFICE
CERTIFICATE OF CORRECTION

PATENT NO. : 4,859,579

DATED : August 22, 1989

INVENTOR(S) : Shigeo Hirano, Tetsuro Kojima, Mitsuru Yamamoto, Noriyuki Inoue and Tatsuo Heki It is certified that error appears in the above-identified patent and that said Letters Patent is hereby corrected as shown below:

In the Abstract, delete " 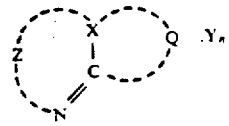 " and insert

-- 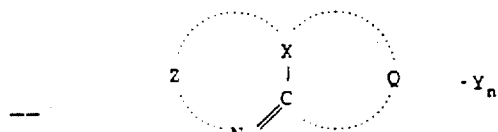 --.

In column 3, line 20, delete " 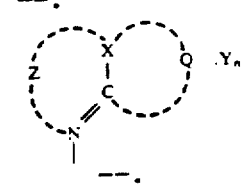 " and insert

-- 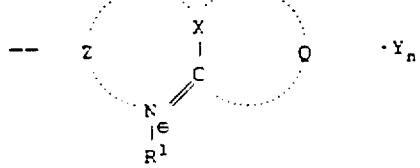 --.

UNITED STATES PATENT AND TRADEMARK OFFICE
CERTIFICATE OF CORRECTION

PATENT NO. : 4,859,579

DATED : August 22, 1989

INVENTOR(S) : Shigeo Hirano, et al.

It is certified that error appears in the above-identified patent and that said Letters Patent is hereby corrected as shown below:

In claim 1, delete " 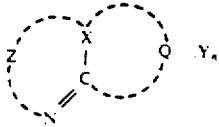 " and insert

-- 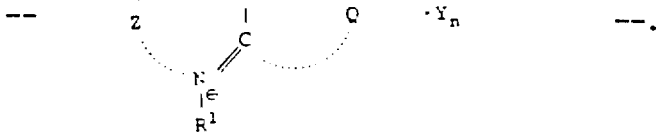 --.

Signed and Sealed this

Fourteenth Day of August, 1990

Attest:

HARRY F. MANBECK, JR.

Attesting Officer     Commissioner of Patents and Trademarks